(12) United States Patent
Dunayevich et al.

(10) Patent No.: US 9,248,123 B2
(45) Date of Patent: Feb. 2, 2016

(54) METHODS OF PROVIDING WEIGHT LOSS THERAPY IN PATIENTS WITH MAJOR DEPRESSION

(75) Inventors: Eduardo Dunayevich, San Diego, CA (US); Gary Tollefson, Indianapolis, IN (US); David Dewitt, legal representative, Indianapolis, IN (US)

(73) Assignee: Orexigen Therapeutics, Inc., La Jolla, CA (US)

( * ) Notice: Subject to any disclaimer, the term of this patent is extended or adjusted under 35 U.S.C. 154(b) by 368 days.

(21) Appl. No.: 12/987,909

(22) Filed: Jan. 10, 2011

(65) Prior Publication Data

US 2011/0172260 A1 Jul. 14, 2011

Related U.S. Application Data

(60) Provisional application No. 61/293,844, filed on Jan. 11, 2010.

(51) Int. Cl.
*A61K 31/485* (2006.01)
*A61K 31/137* (2006.01)
*A61K 31/439* (2006.01)

(52) U.S. Cl.
CPC ............ *A61K 31/439* (2013.01); *A61K 31/485* (2013.01); *Y10S 514/91* (2013.01)

(58) Field of Classification Search
USPC ........................................................ 514/282
See application file for complete search history.

(56) References Cited

U.S. PATENT DOCUMENTS

| | | |
|---|---|---|
| 3,819,706 A | 6/1974 | Mehta |
| 3,885,046 A | 5/1975 | Mehta |
| 3,942,641 A | 3/1976 | Segre |
| 4,089,855 A | 5/1978 | Chatterjie et al. |
| 4,172,896 A | 10/1979 | Uno et al. |
| 4,218,433 A | 8/1980 | Kooichi et al. |
| 4,295,567 A | 10/1981 | Knudsen |
| 4,483,846 A | 11/1984 | Koide et al. |
| 4,513,006 A | 4/1985 | Maryanoff et al. |
| 4,673,679 A | 6/1987 | Aungst et al. |
| 4,689,332 A | 8/1987 | McLaughlin et al. |
| 4,828,836 A | 5/1989 | Elger et al. |
| 4,831,031 A | 5/1989 | Lowe et al. |
| 4,855,306 A | 8/1989 | Markstein et al. |
| 4,895,845 A | 1/1990 | Seed |
| 5,000,886 A | 3/1991 | Lawter et al. |
| 5,028,612 A | 7/1991 | Glover |
| 5,082,864 A | 1/1992 | Van den Oetelaar et al. |
| 5,202,128 A | 4/1993 | Morella et al. |
| 5,213,807 A | 5/1993 | Chemburkar et al. |
| 5,213,808 A | 5/1993 | Bar-Shalom et al. |
| 5,283,263 A | 2/1994 | Norden |
| 5,312,925 A | 5/1994 | Allen et al. |
| 5,358,970 A | 10/1994 | Ruff et al. |
| 5,364,841 A | 11/1994 | Cooper et al. |
| 5,403,595 A | 4/1995 | Kitchell et al. |
| 5,426,112 A | 6/1995 | Zagon et al. |
| 5,427,798 A | 6/1995 | Ludwig et al. |
| 5,486,362 A | 1/1996 | Kitchell et al. |
| 5,512,593 A | 4/1996 | Dante |
| 5,541,231 A | 7/1996 | Ruff et al. |
| 5,626,874 A | 5/1997 | Conte et al. |
| 5,714,519 A | 2/1998 | Cincotta et al. |
| 5,716,976 A | 2/1998 | Bernstein |
| 5,719,197 A | 2/1998 | Kanios et al. |
| 5,731,000 A | 3/1998 | Ruff et al. |
| 5,738,874 A | 4/1998 | Conte et al. |
| 5,763,493 A | 6/1998 | Ruff et al. |
| 5,817,665 A | 10/1998 | Dante |
| 5,817,666 A | 10/1998 | Katz |
| 5,856,332 A | 1/1999 | Dante |
| 5,866,164 A | 2/1999 | Kuczynski et al. |
| 5,948,799 A | 9/1999 | Cropp |
| 5,958,962 A | 9/1999 | Cook |
| 5,977,099 A | 11/1999 | Nickolson |
| 6,004,970 A | 12/1999 | O'Malley et al. |
| 6,033,686 A | 3/2000 | Seth |
| 6,034,091 A | 3/2000 | Dante |
| 6,048,322 A | 4/2000 | Kushida |
| 6,071,537 A | 6/2000 | Shank |
| 6,071,918 A | 6/2000 | Cook |
| 6,087,386 A | 7/2000 | Chen et al. |
| 6,096,341 A | 8/2000 | Seth |
| 6,110,973 A | 8/2000 | Young |
| 6,120,803 A | 9/2000 | Wong et al. |

(Continued)

FOREIGN PATENT DOCUMENTS

| | | |
|---|---|---|
| CA | 2317044 | 7/1999 |
| EP | 0 005 636 | 11/1979 |

(Continued)

OTHER PUBLICATIONS

Padwal (Contrave, a bupropion and naltrexone combination therapy for the potential treatment of obesity, Department of Medicine, University of Iberta Hospital, Curr Opin Investig Drugs Oct. 2009; 10(10):1117-25 Atlantis et al. (Obesity and depression or anxiety, BMJ 2009; 339 published Oct. 6, 2009.*

Atlantis et al. (Obesity and depression or anxiety, BMJ 2009; 339 published Oct. 6, 2009.*

Ackerman et al. 1998. Clinical characteristics of response to fluoxetine treatment of obsessive-compulsive disorder. Journal of Clinical Psychopharmacology, 18(3):185-192.

Altman et al. (2005) Standard Deviations and Standard Errors, BMJ, 331:903.

(Continued)

*Primary Examiner* — Savitha Rao
*Assistant Examiner* — Gregg Polansky
(74) *Attorney, Agent, or Firm* — Knobbe, Martens, Olson & Bear, LLP

(57) ABSTRACT

Disclosed are methods of providing weight loss therapy, particularly for patients suffering from major depression.

18 Claims, No Drawings

(56) References Cited

U.S. PATENT DOCUMENTS

| | | |
|---|---|---|
| 6,143,327 A | 11/2000 | Seth |
| 6,150,366 A | 11/2000 | Arenson et al. |
| 6,153,223 A | 11/2000 | Apelian et al. |
| 6,183,778 B1 | 2/2001 | Conte et al. |
| 6,191,117 B1 | 2/2001 | Kozachuk |
| 6,197,827 B1 | 3/2001 | Cary |
| 6,210,716 B1 | 4/2001 | Chen et al. |
| 6,238,697 B1 | 5/2001 | Kumar et al. |
| 6,245,766 B1 | 6/2001 | Watsky |
| 6,248,363 B1 | 6/2001 | Patel et al. |
| 6,262,049 B1 | 7/2001 | Coffin et al. |
| 6,274,579 B1 | 8/2001 | Morgan et al. |
| 6,294,192 B1 | 9/2001 | Patel et al. |
| 6,306,436 B1 | 10/2001 | Chungi et al. |
| 6,323,236 B2 | 11/2001 | McElroy |
| 6,342,496 B1 | 1/2002 | Jerussi et al. |
| 6,342,515 B1 | 1/2002 | Masuda et al. |
| 6,344,474 B1 | 2/2002 | Maruani et al. |
| 6,369,113 B2 | 4/2002 | Young |
| 6,383,471 B1 | 5/2002 | Chen et al. |
| 6,387,956 B1 | 5/2002 | Shapira |
| 6,420,369 B1 | 7/2002 | Marcotte |
| 6,437,147 B1 | 8/2002 | Andersen et al. |
| 6,441,038 B1 | 8/2002 | Loder et al. |
| 6,451,860 B1 | 9/2002 | Young |
| 6,462,237 B1 | 10/2002 | Gidwani et al. |
| 6,500,459 B1 | 12/2002 | Chhabra et al. |
| 6,506,799 B1 | 1/2003 | Dasseux |
| 6,514,531 B1 | 2/2003 | Alaux et al. |
| 6,528,520 B2 | 3/2003 | Clemens |
| 6,541,478 B1 | 4/2003 | O'Malley et al. |
| 6,548,551 B2 | 4/2003 | Hinz |
| 6,569,449 B1 | 5/2003 | Stinchcomb et al. |
| 6,576,256 B2 | 6/2003 | Liang et al. |
| 6,589,553 B2 | 7/2003 | Li et al. |
| 6,622,036 B1 | 9/2003 | Suffin |
| 6,627,223 B2 | 9/2003 | Percel et al. |
| 6,630,165 B2 | 10/2003 | Seroff et al. |
| 6,638,535 B2 | 10/2003 | Lemmens et al. |
| 6,652,882 B1 | 11/2003 | Odidi et al. |
| 6,682,759 B2 | 1/2004 | Lim et al. |
| 6,686,337 B2 | 2/2004 | Connor |
| 6,702,097 B1 | 3/2004 | Leidy et al. |
| 6,706,283 B1 | 3/2004 | Appel et al. |
| 6,713,488 B2 | 3/2004 | Sadee et al. |
| 6,797,283 B1 | 9/2004 | Edgren et al. |
| 6,893,660 B2 | 5/2005 | Li et al. |
| 6,893,661 B1 | 5/2005 | Odidi et al. |
| 6,905,708 B2 | 6/2005 | Li et al. |
| 6,923,988 B2 | 8/2005 | Patel et al. |
| 6,926,907 B2 | 8/2005 | Plachetka |
| 6,995,169 B2 | 2/2006 | Chapleo et al. |
| 7,109,198 B2 | 9/2006 | Gadde et al. |
| 7,375,111 B2 | 5/2008 | Weber et al. |
| 7,422,110 B2 | 9/2008 | Zanden et al. |
| 7,425,571 B2 | 9/2008 | Gadde et al. |
| 7,429,580 B2 | 9/2008 | Gadde et al. |
| 7,462,626 B2 | 12/2008 | Weber et al. |
| 7,682,633 B2 | 3/2010 | Matthews et al. |
| 7,754,748 B2 | 7/2010 | Gadde et al. |
| 8,318,788 B2 | 11/2012 | McKinney et al. |
| 8,969,371 B1 | 3/2015 | Klassen et al. |
| 9,107,837 B2 | 8/2015 | McKinney et al. |
| 2001/0025038 A1 | 9/2001 | Coffin et al. |
| 2001/0046964 A1 | 11/2001 | Percel et al. |
| 2002/0012680 A1 | 1/2002 | Patel et al. |
| 2002/0019364 A1 | 2/2002 | Renshaw |
| 2002/0022054 A1 | 2/2002 | Sawada et al. |
| 2002/0025972 A1 | 2/2002 | Hintz |
| 2002/0037836 A1 | 3/2002 | Henriksen |
| 2002/0044962 A1 | 4/2002 | Cherukuri et al. |
| 2002/0055512 A1 | 5/2002 | Marin et al. |
| 2002/0090615 A1 | 7/2002 | Rosen et al. |
| 2002/0198227 A1 | 12/2002 | Bernstein |
| 2003/0003151 A1 | 1/2003 | Chopra |
| 2003/0017189 A1 | 1/2003 | Wong et al. |
| 2003/0035840 A1 | 2/2003 | Li et al. |
| 2003/0044462 A1 | 3/2003 | Subramanian et al. |
| 2003/0054031 A1 | 3/2003 | Li et al. |
| 2003/0054041 A1 | 3/2003 | Lemmens et al. |
| 2003/0055008 A1 | 3/2003 | Marcotte |
| 2003/0055038 A1 | 3/2003 | Howard et al. |
| 2003/0068371 A1 | 4/2003 | Oshlack et al. |
| 2003/0087896 A1 | 5/2003 | Glover |
| 2003/0091630 A1 | 5/2003 | Louie-Helm et al. |
| 2003/0109546 A1 | 6/2003 | Fenton |
| 2003/0130322 A1 | 7/2003 | Howard |
| 2003/0133982 A1 | 7/2003 | Heimlich et al. |
| 2003/0133985 A1 | 7/2003 | Louie-Helm et al. |
| 2003/0135056 A1 | 7/2003 | Andersen et al. |
| 2003/0144174 A1 | 7/2003 | Brenna et al. |
| 2003/0144271 A1 | 7/2003 | Shulman |
| 2003/0147952 A1 | 8/2003 | Lim et al. |
| 2003/0161874 A1 | 8/2003 | Li et al. |
| 2003/0198683 A1 | 10/2003 | Li et al. |
| 2003/0215496 A1 | 11/2003 | Patel et al. |
| 2004/0002462 A1 | 1/2004 | Najarian |
| 2004/0005368 A1* | 1/2004 | Mann et al. .................. 424/725 |
| 2004/0022852 A1 | 2/2004 | Chopra |
| 2004/0029941 A1 | 2/2004 | Jennings |
| 2004/0047908 A1 | 3/2004 | Lemmens et al. |
| 2004/0059241 A1 | 3/2004 | Suffin |
| 2004/0092504 A1 | 5/2004 | Benja-Athon |
| 2004/0096499 A1 | 5/2004 | Vaya et al. |
| 2004/0101556 A1 | 5/2004 | Li et al. |
| 2004/0105778 A1 | 6/2004 | Lee et al. |
| 2004/0106576 A1 | 6/2004 | Jerussi et al. |
| 2004/0115134 A1 | 6/2004 | Merisko-Liversidge |
| 2004/0122033 A1 | 6/2004 | Nargund et al. |
| 2004/0158194 A1 | 8/2004 | Wolff et al. |
| 2004/0185097 A1 | 9/2004 | Kannan et al. |
| 2004/0204472 A1* | 10/2004 | Briggs et al. .................. 514/406 |
| 2004/0228915 A1 | 11/2004 | Noack et al. |
| 2004/0228924 A1 | 11/2004 | Oshlack et al. |
| 2004/0242974 A1 | 12/2004 | Glover |
| 2004/0258757 A1 | 12/2004 | Bosch et al. |
| 2005/0004106 A1 | 1/2005 | Romano |
| 2005/0013863 A1 | 1/2005 | Lim et al. |
| 2005/0019385 A1 | 1/2005 | Houze |
| 2005/0019409 A1 | 1/2005 | Edgren et al. |
| 2005/0019412 A1 | 1/2005 | Bosch et al. |
| 2005/0026977 A1 | 2/2005 | Jennings |
| 2005/0026986 A1 | 2/2005 | Maruani et al. |
| 2005/0031691 A1 | 2/2005 | McGurk et al. |
| 2005/0043704 A1 | 2/2005 | Lieberburg |
| 2005/0043705 A1 | 2/2005 | Lieberburg |
| 2005/0043773 A1 | 2/2005 | Lieberburg |
| 2005/0063913 A1 | 3/2005 | Pruitt et al. |
| 2005/0096311 A1 | 5/2005 | Suffin et al. |
| 2005/0112198 A1 | 5/2005 | Challapalli et al. |
| 2005/0112211 A1 | 5/2005 | Gervais et al. |
| 2005/0118268 A1 | 6/2005 | Percel et al. |
| 2005/0137144 A1 | 6/2005 | Gadde et al. |
| 2005/0142195 A1 | 6/2005 | Li et al. |
| 2005/0143322 A1 | 6/2005 | Gadde et al. |
| 2005/0147664 A1 | 7/2005 | Liversidge et al. |
| 2005/0154002 A1 | 7/2005 | Crooks et al. |
| 2005/0163840 A1 | 7/2005 | Sawada et al. |
| 2005/0181049 A1 | 8/2005 | Dong et al. |
| 2005/0214368 A1 | 9/2005 | Kawakami et al. |
| 2005/0214371 A1 | 9/2005 | Di Capua et al. |
| 2005/0214372 A1 | 9/2005 | Di Capua et al. |
| 2005/0215552 A1 | 9/2005 | Gadde et al. |
| 2005/0232990 A1 | 10/2005 | Boehm et al. |
| 2005/0238718 A1 | 10/2005 | Oberegger et al. |
| 2005/0245460 A1 | 11/2005 | Meyerson et al. |
| 2005/0250838 A1 | 11/2005 | Challapalli et al. |
| 2005/0277579 A1 | 12/2005 | Gadde et al. |
| 2006/0009514 A1 | 1/2006 | Gadde et al. |
| 2006/0018933 A1 | 1/2006 | Vaya et al. |
| 2006/0018934 A1 | 1/2006 | Vaya et al. |
| 2006/0024365 A1 | 2/2006 | Vaya et al. |
| 2006/0051418 A1 | 3/2006 | Cowen et al. |
| 2006/0058293 A1 | 3/2006 | Weber et al. |

(56) References Cited

U.S. PATENT DOCUMENTS

| | | |
|---|---|---|
| 2006/0069086 A1 | 3/2006 | Michalow |
| 2006/0079501 A1 | 4/2006 | Gadde et al. |
| 2006/0100205 A1 | 5/2006 | Weber et al. |
| 2006/0122127 A1 | 6/2006 | Rao et al. |
| 2006/0142290 A1 | 6/2006 | Weber et al. |
| 2006/0160750 A1 | 7/2006 | Gadde et al. |
| 2006/0246131 A1 | 11/2006 | Cottinham |
| 2006/0276412 A1 | 12/2006 | Tollefson |
| 2007/0078135 A1 | 4/2007 | Yuan et al. |
| 2007/0099947 A1 | 5/2007 | Dean et al. |
| 2007/0117827 A1 | 5/2007 | Tollefson et al. |
| 2007/0128298 A1 | 6/2007 | Cowley et al. |
| 2007/0129283 A1 | 6/2007 | McKinney et al. |
| 2007/0148237 A1 | 6/2007 | McKinney et al. |
| 2007/0149451 A1 | 6/2007 | Holmes |
| 2007/0179168 A1 | 8/2007 | Cowley et al. |
| 2007/0185084 A1 | 8/2007 | McKinney et al. |
| 2007/0270450 A1 | 11/2007 | Weber et al. |
| 2007/0275970 A1 | 11/2007 | Weber et al. |
| 2007/0281021 A1* | 12/2007 | McKinney et al. ........... 424/468 |
| 2008/0027487 A1 | 1/2008 | Patel et al. |
| 2008/0058407 A1 | 3/2008 | Baron et al. |
| 2008/0110792 A1 | 5/2008 | McKinney et al. |
| 2008/0113026 A1 | 5/2008 | McKinney et al. |
| 2008/0214592 A1 | 9/2008 | Cowley et al. |
| 2009/0018115 A1 | 1/2009 | Gadde et al. |
| 2009/0076108 A1 | 3/2009 | Gadde et al. |
| 2010/0166889 A1 | 7/2010 | Sanfilippo |
| 2010/0190793 A1 | 7/2010 | Weber et al. |
| 2011/0028505 A1 | 2/2011 | McKinney et al. |
| 2011/0059170 A1 | 3/2011 | McKinney et al. |
| 2011/0098289 A1 | 4/2011 | Gadde et al. |
| 2011/0144145 A1 | 6/2011 | Tollefson |
| 2011/0172260 A1 | 7/2011 | Dunayevich et al. |
| 2012/0010232 A1 | 1/2012 | Weber et al. |
| 2013/0177602 A1 | 7/2013 | McKinney et al. |
| 2013/0245055 A1 | 9/2013 | Wright et al. |
| 2014/0080857 A1 | 3/2014 | McKinney et al. |
| 2014/0322318 A1 | 10/2014 | McKinney et al. |
| 2014/0364468 A1 | 12/2014 | Gadde et al. |
| 2015/0119417 A1 | 4/2015 | Tollefson |
| 2015/0141452 A1 | 5/2015 | Weber et al. |
| 2015/0164806 A1 | 6/2015 | McKinney et al. |
| 2015/0182524 A1 | 7/2015 | Klassen et al. |

FOREIGN PATENT DOCUMENTS

| | | |
|---|---|---|
| EP | 0 294 028 | 12/1988 |
| EP | 0 442 769 | 8/1991 |
| EP | 0 541 192 | 5/1993 |
| EP | 0 598 309 | 5/1994 |
| EP | 1 275 373 | 1/2003 |
| EP | 1 759 701 | 7/2007 |
| EP | 1 813 276 | 8/2007 |
| JP | 2003-509349 | 3/2003 |
| RU | 2214241 | 10/2003 |
| WO | WO 83/03197 | 9/1983 |
| WO | WO 90/13294 | 11/1990 |
| WO | WO 94/20100 | 9/1994 |
| WO | WO 96/09047 | 3/1996 |
| WO | WO 97/06786 | 2/1997 |
| WO | WO 97/06787 | 2/1997 |
| WO | WO 97/41873 | 11/1997 |
| WO | WO 98/00130 | 1/1998 |
| WO | WO 99/16375 | 4/1999 |
| WO | WO 99/37305 | 7/1999 |
| WO | WO 99/38504 | 8/1999 |
| WO | WO 00/50020 | 8/2000 |
| WO | WO 00/51546 | 9/2000 |
| WO | WO 00/61139 | 10/2000 |
| WO | WO 00/62757 | 10/2000 |
| WO | WO 00/76493 | 12/2000 |
| WO | WO 01/01973 | 1/2001 |
| WO | WO 01/26641 | 4/2001 |
| WO | WO 01/52833 | 7/2001 |
| WO | WO 01/52851 | 7/2001 |
| WO | WO 01/58447 | 8/2001 |
| WO | WO 01/58451 | 8/2001 |
| WO | WO 01/62257 | 8/2001 |
| WO | WO 01/78725 | 10/2001 |
| WO | WO 01/85257 | 11/2001 |
| WO | WO 02/09694 | 2/2002 |
| WO | WO 02/24214 | 3/2002 |
| WO | WO 02/087590 | 11/2002 |
| WO | WO 03/013524 | 2/2003 |
| WO | WO 03/013525 | 2/2003 |
| WO | WO 03/013479 | 3/2003 |
| WO | WO 03/092682 | 11/2003 |
| WO | WO 03/097051 | 11/2003 |
| WO | WO 2004/002463 | 1/2004 |
| WO | WO 2004/009015 | 1/2004 |
| WO | WO 2004/024096 | 3/2004 |
| WO | WO 2004/052289 | 6/2004 |
| WO | WO 2004/054570 | 7/2004 |
| WO | WO 2004/054571 | 7/2004 |
| WO | WO 2004/071423 | 8/2004 |
| WO | WO 2004/091593 | 10/2004 |
| WO | WO 2004/100956 | 11/2004 |
| WO | WO 2004/100992 | 11/2004 |
| WO | WO 2004/110368 | 12/2004 |
| WO | WO 2004/110375 | 12/2004 |
| WO | WO 2005/000217 | 1/2005 |
| WO | WO 2005/077362 | 2/2005 |
| WO | WO 2005/032555 | 4/2005 |
| WO | WO 2005/049043 | 6/2005 |
| WO | WO 2005/070641 | 8/2005 |
| WO | WO 2005/079773 | 9/2005 |
| WO | WO 2005/089486 | 9/2005 |
| WO | WO 2006/049941 | 5/2006 |
| WO | WO 2006/052542 | 5/2006 |
| WO | WO 2006/055854 | 5/2006 |
| WO | WO 2006/088748 | 8/2006 |
| WO | WO 2007/012064 | 1/2007 |
| WO | WO 2007/047351 | 4/2007 |
| WO | WO 2007/085637 | 8/2007 |
| WO | WO 2008/119978 | 10/2008 |
| WO | WO 2009/158114 | 12/2009 |
| WO | WO 2013/184837 | 12/2013 |

OTHER PUBLICATIONS

Anderson et al. (2002) Bupropion SR enhances weight loss, Obesity R., 10(7):633-641.

Appolinario et al. (2004) Pharmacological Approaches in the Treatment of Binge Eating Disorder, Current Drug Targets, 5:301-307.

Aronne et al. (2003) Weight gain in the treatment of mood disorders, J. Clin Psychiatry, 64(suppl 9).

Asconape, 2002, Some Common Issues in the Use of Antiepileptic Drugs, Seminars in Neurology; 22(1):27-39.

Astrup et al. (Mar. 1991) Thermogenic Synergism Between Ephedrine and Caffeine in Healthy Volunteers: A Double-Blind, Placebo-Controlled Study, Metabolism, 40(3):323-329.

Atkinson (2003) Clinical Guidelines on the identification, Evaluation, and pharmacologic treatment of obesity in Adults, Online, 07-25, URL:http://www.endotext.org.obesity/obesity15b/obesity15b.htm.

Atkinson et al. (Oct. 1985) Effects of long-term therapy with naltrexone on body weight in obesity, Clinical Pharmacology & Therapeutics, 38:419-422.

Ayala (2000) Weight Loss Associated With the Administration of Zonisamide, AES Proceedings, Epilepsia 41(Suppl. 7) :99—No. 2.041.

Ayala et al., Dec. 1-6, 2000, Weight loss associated with the administration of zonisamide, a compendium of posters and platform session for ZonegranTM and Diastat®, Annual Meeting 2000 of the American Epilepsy Society, Los Angeles, CA.

Baldassano et al. (2006) Acute treatment of bipolar depression with adjunctive zonisamide: a retrospective chart review, Disorders 6:432-434.

Barr et al. 1993. The serotonin hypothesis of obsessive compulsive disorder. International Clinical Psychopharmacology, 8(2):79-82.

(56) References Cited

OTHER PUBLICATIONS

Bastani et al. 1991. Serotonin uptake and imipramine binding in the blood platelets of obsessive-compulsive disorder patients. Biol. Psychiatry, 30:131-139.

Beelen et al. (2001) Asymptomatic QTC prolongation associated with queitiapine fumarate overdose in a patient being treated with risperidone, Human & Experimental Toxicology 20:215-219.

Benjamin et al. 1993. Naltrexone and fluoxetine in Prader-Willi syndrome. J. Am. Acad. Child Adolesc. Psychiatry, 32(4):870-873.

Bergeron et al. 2002. Sertraline and fluoxetine treatment of obsessive-compulsive disorder: Results of a double-blind, 6-month treatment study. Journal of Clinical Psychopharmacology, 22(2):148-154.

Berke et al. (Jul. 15, 2000) Medical Management of Obesity, American Academy of Family Physicians, 62(2):419-26 Abstract.

Billett et al. 1997. Obsessive compulsive disorder, response to serotonin reuptake inhibitors and the serotonin transporter gene. Molecular Psychiatry, 2:403-406.

Blanchard et al. (2003) Pancreatitis Treated with Didanosine and Tenofabir Disoproxil Fumarate Clinical Infectious Diseases, 37:57-62.

Broocks et al. 1998. Higher prevalence of obsessive-compulsive symptoms in patients with blepharospasm than in patients with hemifacial spasm. Am. J. Psychiatry, 155:555-557.

Bupropion (Oral Route), MayoClinic.com, 19 pp., 2009.

Calabrese et al. (Sep. 2000) Letters to the Editors, Lamotrigine and Clozapine for Bipolar Disorder, American J. of Psychiatry, 157:1523.

Carlsen et al. (Jan. 1998) Evidence for dissociation of insulin- and weight-reducing effects of metformin in non-diabetic male patients with coronary heart disease, Diabetes Research and Clinical Practice Amersterdam, 39(1):47-54.

Carpenter et al. (Jan. 1, 1999) Mirtazapine Augmentation in the Treatment of Refractory Depression, J Clin Psychiatry, 60:1.

Carrion, 1995. Naltrexone for the treatment of trichotillomania: A case report. J. Clin. Psychopharmacol., 15(6):444-445.

Carroll (2003) Medicinal Chemistry Division Award Address: Monoamine Transporters and Opioid Receptors. Targets for Addiction Therapy, J. Med. Chem; 46(10)1775-1794.

Carter et al. 2003. Pharmacologic treatment of binge-eating disorder. Primary Psychiatry, 10(10)31-36.

Cash et al. (2000) Attitudes about antidepressants: Influence of information about weight-related side effects, Perceptual and Motor Skills, 90:453-456.

Casner et al. 1996. Naltrexone and self-injurious behavior: A retrospective population study. Journal of Clinical Psychopharmacology, 16(5):389-394.

Chen et al. (Jan. 2004) Synergistic Effects of Cannabiniod inverse agonist AM251 and opioid antagonist namefene on food intake, Brain Res, 999:22-230.

Chengappa et al. (2002) Changes in body Weight and Body mass index among psychiatric patients receiving lithium, valproate, or topiramate: an open-label, nonrandomized chart review, Clinical Therapeutics, 24(10):1576-1584.

Ching, Mar. 1980, Influence of diphenylhydantoin upon oral glucose tolerance test in obesity, Chinese Medical Journal, 27(1):432-439.

Chouinard et al. 1996. Potentiation of fluoxetine by aminoglutethimide, an adrenal steroid suppressant, in obsessive-compulsive disorder resistant to SSRIs: A case report. Prog. Neuro-Psychopharmacol. & Biol. Psychiat., 20:1067-1079.

Clapham et al. (2001) Anti-obesity drugs: a critical review of current therapies and future opportunities. Pharmacology & Therapeutics. 89:81-121.

Clark et al., 2003, Diabetes mellitus associated with atypical antipsychotic medications, Diabetes Technology & Therapeutics, 5(4):669-683.

Clinical Trial: Drug Treatment for Depressed Alcoholics (Naltrexone/Fluoxetine). (n.d.) Retrieved Jun. 28, 2007, from http://www.clinicaltrials.gov/ct/show/NCT00006204;jsessionid+FED6D0856E098BC0B1940E464179B71B?order=28.

Colosimo, et al. 1999. Motor fluctuations in Parkinson's disease: Pathophysiology and treatment. European Journal of Neurology, 6:1-21.

Cone et al. (2001) The arcuate nucleus as a conduit for diverse signals relevant to energy homeostasis, Int'l Journal of Obesity, 25(5):S63-S67.

Croft et al. (Apr. 2002) Effect on body weight of bupropion sustained-release in patients with major depression treated for 52 weeks, Clinical Therapeutics 24(4):662-672.

Dechant et al. (1991) Drugs, 41:225-253.

Dembowski et al. (2003) Successful Antimanic Treatment and Mood Stabilization with Lamotrigine, Clozapine, and Valproate in a Bipolar Patient after Lithium-induced Cerebellar Deterioration, Letter Pharmacopsychiatry, 36:83-86.

Deshmukh et al. (Jul. 2003) Managing weight gain as a side effect of antidepressant therapy, Cleveland Clinic Journal of Medicine, vol. 70.

DeSimone et al. (2005) Carbonic anhydrase inhibitors. Zonisamide is an effective inhibitor of the cytosolic isozyme II and mitochondrial isozyme V: Solution and x-ray crystallographic studies, Bioorganic & Medicinal Chemistry Letters, 15:2315-2320

Devlin et al. (2000) Open treatment of overweight binge eaters with phentermine and fluoxetine as an adjunct to cognitive-behavioral therapy. Int. J. Eating Disord; 28:325-332.

Sleep Disorders, in Diagnostic and Statistical Manual of Mental Disorders, 4th Edition, American Psychiatric Association, p. 583-595 (2000).

Dursen et al. (Oct. 1999) Clozapine Plus Lamotrigine in Treatment-Resistant Schizophrenia, Arch Gen Psychiatry, 56:950-951.

Dursun et al. (2001) Accelerated Weight Loss After Treating Refractory Depression with Fluoxetine Plus Topiramate: Possible Mechanism of Action, Canadian Journal of Psychiatry, 46(3):287-288.

Dursun et al. (2001) Augmenting Antipsychotic treatment with Lamotrigine or topiramate in patients with treatment-resistant Schizophrenia: a naturalistic case-series outcome study Journal of Psychopharmacology 15(4):297-301.

Dursun et al. (2001) Psychopharmacology for the Clinician Psychopharmacologie Pratiqu, Journal of Psychiatry Neuroscience, 26(2):168.

Dursun et al. (Winter 2002) Lamotrgine-Clozapine Combination in Refractory Schizophrenia: Three Cases, J. Neuropsychiatry Clin. Neuroscience, 14:1:86.

Dwyer et al., 2002, Psychoactive drugs affect glucose transport and the regulation of glucose metabolism, International Review of Neurobiology, 51:503-530.

El-Haschimi et al. 2000. Two defects contribute to hypothalamic leptin resistance in mice with diet-induced induced obesity. The Journal of Clinical Investigation, 105(12):1827-1832.

Erez et al., 1982, Narcotic antagonistic potency of bivalent ligands which contain β-naltrexamine. Evidence for bridging between proximal recognition sites, J. Med. Chem., 25:847-849.

Erfuth et al. (Mar. 2002) Bupropion as add-on strategy in difficult-to-treat bipolar depressive patients, Neurophsychobiology, 45(Supplement 1):33-36.

Erzegovesi et al. 2001. Clinical predictors of drug response in obsessive-compulsive disorder. Journal of Clinical Psychopharmacology, 21(5):488-492.

Esposito-Avella et al. (Jan. 1973) Studies on the protective effect of diphenylhyndantoin against alioxan diabetes in mice, Proceedings of the Society for Experimental Biology & Medicine, 142(1):82-85.

Ettmayer et al, May 6, 2004, Lessons learned from marketed and investigational prodrugs, J. Med. Chem, 47(10):2393-2404.

Faught et al. (2001) Randomized Controlled Trial of Zonisamide for the Treatment of Refractory Partial-Onset Seizures., Neurology; 57(10):1774-1779.

Fava, Maurizio (2000) Weight Gain and Antidepressants. J Clin Psychiatry; 61(suppl 11):37-41.

Ferre et al. (1996) Correction of diabetic alterations by glucokinase. Proc. Natl. Acad. Sci. USA, 93:7225-7230.

Ferre et al. (1996) Evidence from transgenic mice that glucokinase is rate limiting for glucose utilization in the liver, The FASEB Journal, 10:1213-1218.

(56) References Cited

OTHER PUBLICATIONS

Fingl et al., The Pharmacological Basis of Therapeutics. Chapter 1: General Principles, pp. 1-46 (1975).
Fontela et al., Mar. 1986, Blocking effect of naloxone, dihydroergotamine and adrenalectomy in lithium-induced hyperglycaemia and glucose intolerance in the rate, Acta Endocrinologica, 111(3):342-348 (abstract).
Fukagawa et al. (Nov. 2001) Monoaminergic anorectic agents, Nippon Yikurigaku Zasshi, 118(5):303-8, 2001 Abstract.
Fulghesu et al. (Aug. 1993) Long-term naltrexone treatment reduces the exaggerated insulin secretion in patients with polycystic ovary disease, Obstetrics & Gynecology, 82(2):191-197.
Fuller et al. (1989) Fluoxetine: A Serotonergic Appetite Suppressant Drug, Drug Development Research, 17(1):1-15.
Gadde et al., 2002, Randomized controlled trial of zonisamide for treating obesity, Epilepsia 43 Suppl. 7:218 (abstract).
Gadde et al, "Zonisamide in Obesity: A 16-Week Randomized Trial", No. NR473, New Research, American Psychiatric Association 2002 Annual Meeting, May 18-23, 2002, Philadelphia, Pennsylvania (abstract).
Gadde et al, Randomized Trial of Weight Loss Efficacy of Zonisamide, No. 304, 26(Suppl. 1), Journal of the International Association for the Study of Obesity, Ninth International Congress on Obesity, Sao Paolo, Brazil, Aug. 24-29, 2002.
Gadde et al. "Bupropion for Weight Loss: An Investigation of Efficacy and Tolerability in Overweight and Obese Women" Obesity Reseach 9 (9): 544-551 (2001).
Gadde et al. (2003) Zonisamide enhances weight loss in patients with obesity: Inpharma; 1383/84:9.
Gadde et al. , "Zonisamide for Weight Loss in Obese Adults—A Randomized Controlled Trial" JAMA 289 (14): 1820-1825 (2003).
Gadde et al., May 1999, Bupropion Sustained Release in Obesity: A Randomized Double-Blind, Placebo-Controlled Study, No. NR634, New Research Program & Abstracts, American Psychiatric Association, 1999 Annual Meeting, The Clinician, Washington, D.C.
Gadde et al., Sep. 1999, A randomized double-blind placebo-controlled study of bupropion sustained release in obesity, European Neuropsychopharmacology, 9(5):366.
Gatley et al. (1996) $^{123}$I-labeled AM251: a radioiodinated ligand which binds in vivo to mouse brain cannabinoid $CB_1$ receptors. European Journal of Pharmacology; 307:331-338.
Gehlert et al. (Oct. 1998) The Selective Norepinephrine Reuptake Inhibitor, LY368975, Reduces Food Consumption in Animal Models of Feeding, J. Pharmacology and Experimental Therapeutics, 87(1):122-7 Abstract.
Gerich et al. (1972) In vitro inhibition of pancreative glucagon secretion by diphenylhydantoin, Journal of Clinical Endocrinology and Metabolism 35(6):823-823.
Gerra et al. 1995. Hostility in heroin abusers subtypes: Fluoxetine and naltrexone treatment. Prog. Neuro-Psychopharmacol. & Biol. Psychiat., 19:1225-1237.
Gerra et al., Sep. 30, 2006, Effects of olanzapine on aggressiveness in heroin dependent patients, Progress in Neuro-Psychopharmacology & Biological Psychiatry, 30(7):1291-1298.
Ginsberg et al. (2000) Effects of Mood Stabilizers on Weight, Primary Psychiatry 7(5):49-58.
Givens et al. (1987) Reduction of hyperinsulinemia and insulin resistance by opiate receptor blockade in the polycystic ovary syndrome with acanthosis nigricans, Journal of Clinical Endocrinology and Metabolism, 64(2):377-382.
Glass et al. (1999) Opioids and food intake: distributed functional neural pathways? Neuropeptides; 33(5):360-368.
Grunenthal, Neo-Eunomin Gebrauschsinformation, Neunomin Prescription Information, Feb. 2004, pp. 1-2.
Goldstein et al. (Mar. 1994) Fluoxetine: a randomized clinical trial in the treatment of obesity, International Journal of Obesity and Related Metabolic Disorders, 17(3):129-135, CAS accession #9424430.
Goodman et al. 1989. The Yale-Brown obsessive compulsive scale. Arch. Gen. Psychiatry, 46:1006-1011.
Gordon et al. (Jun. 1999) Mood Stablization and Weight Loss with Topiramate American Journal of Psychiatry, American Psychiatric Association, Washington D.C., 156(6):968-969.
Grady (Mar. 15, 2003) Quest for Weight-Loss Drug Takes an Unusual Turn, The New York Times—Health, www.nytimes.com, 3 pp.
Grant et al. 2004. Impulse control disorders: Clinical characteristics and pharmacological management. Annals of Clinical Psychiatry, 16:27-34.
Grant et al. 2004. Pharmacotherapy outcome in older pathological gamblers: A preliminary investigation. Journal of Geriatric Psychiatry and Neurology, 17(1):9-12.
Grant et al. 2006. Compulsive aspects of impulse-control disorders. Psychiatr. Clin. North Am., 29(2):539-x.
Greenberg et al. 1998. Delayed obsessive-compulsive disorder symptom exacerbation after a single dose of a serotonin antagonist in fluoxetine-treated but not untreated patients. Psychopharmacology, 140:434-444.
Greenway et al. (2000) A Long-acting Leptin Analog does not Enhance Fat, Visceral Fat, or Weight Loss When Combined with Caffeine Ephedrine in Obese Subjects, International Journal of Obesity, S136.
Greenway et al. (Jul. 1999) Double-Blind, Randomized, Placebo-Controlled Clinical Trials with Non-prescription Medications for the Treatment of Obesity, Obesity Research, 7(4):370-78.
Greist et al. (Apr. 1995) Double-blind Parallel Comparison of Three Dosages of Sertraline and Placebo in Outpatients With Obsessive-compulsive Disorder, Arch Gen Psychiatry, 52:289-295.
Hahn et al. (1985) Irreversible opiate agonists and antagonists. III. Phenylhydrazone derivatives of naloxone and oxymorphone. J. Pharm. Exper. Therapeutics; 235:846-850.
Hamidi et al. 2007. Naltrexone in obsessive-compulsive disorder: An open-label trial. Iranian Journal of Psychiatry and Behavioral Sciences, 1(1):16-21.
Harrison's Principles of Internal Medicine, Braunwald et al., The epilepsies and convulsive disorders, Eleventh Edition, McGraw-Hill Book Company, pp. 1921-1930 (1987).
Hashiguti et al. (1993) Simultaneous determination of in vivo hydroxylation of tyrosine and tryptophan in rat striatum by microdialysis-HPLC: relationship between dopamine and serotonin biosynthesis; Journal of Neural Transmission, 93:213-223.
Hollander et al. 1991. Effects of chronic fluoxetine treatment on behavioral and neuroendocrine responses to meta-chlorophenylpiperazine in obsessive-compulsive disorder. Psychiatry Research, 36:1-17.
Hussey et al., 2002, Synthesis of a β-estradiol-biotin chimera that potently heterodimerizes estrogen receptor and streptavidin proteins in a yeast three-hybrid system, J. Am. Chem. Soc., 125:3692-3693.
Insulin Resistance and Pre-diabetes, http://diabetes.niddk.hih.gov/DM/pubs/insulineresistance/, NIH Publication No. 09/4893, Oct. 2008, 9 pp.
Islam et al., 1994, Naltrexone, Serotonin Receptor Subtype Antagonists, and Carbohydrate Intake in Rats, Pharmacology Biochemistry and Behavior, 48(1):193-201.
Jain et al. (Oct. 2002) Bupropin SR vs. Placebo for Weight Loss in Obese Patients with Depressive Symptoms, Obesity Research, 10:1049-56.
Jallon et al. (2001) Bodyweight gain and anticonvulsants: a comparative review. Drug Safety; 24(13):969-978.
Japanese Journal of Clinical Psychiatry (1987 16(1):123-132), and English-language version of Japanese Office Action citing the same (dated Oct. 28, 2008).
Kanba et al. (1994) The first open study of zonisamide, a novel anticonvulsant, shows efficacy in mania. Progress in Neuro-Psychopharmacology and Biological Psychiatry; 18(4):707-715.
Kim et al. 1990. Open fixed dose trial of fluoxetine in the treatment of obsessive compulsive disorder. Drug Development Research, 19:315-319.
Kimura et al., 1992, Pharmacokinetic interaction of zonisamide in rats: effects of other antiepileptics on zonisamide, J. Pharmacobio-Dyn. 15:631-639.
Kiptoo et al. (2006) Enhancement of Transdermal delivery or 6-B-naltrexol via a codrug linked to hydroxyburpropion, Journal of Controlled Release 113:137-145.

(56) References Cited

OTHER PUBLICATIONS

Kirkham et al. (2001) Synergistic effects of opioid and cannabinoid antagonists on food intake. Psychopharmacology; 153:267-270.
Kirov et al. (2003) Add-on topiramate reduces weight in overweight patients with affective disorders: a clinical case. BMC Psychiatry, 5:19, 8 pp.
Klok et al., 2002, Cholesteryl-(l-lactic acid)n. building blocks for self-assembling biomaterials, Macromolecules, 35:746-759.
Kolb et al. (1985) Synthesis and Pharmacological Characterization of Fluorescent Opioid Receptor Probes. A. Pharmaceutical Res, 2(6):266-271.
Korner et al. (2003) The emerging science of body weight regulation and its impact on obesity treatment, J. Clin. Invest. 111(5):565-570.
Kossard, et al. 2006. Defining urticarial dermatitis: A subset of dermal hypersensitivity reaction pattern. Arch. Dermatol., 142:29-34.
Krauss et al. 1997. Tics secondary to craniocerebral trauma, Movement Disorders, 12(5):776-782.
Krupitsky et al. 2006. Naltrexone with or without fluoxetine for preventing relapse to heroin addiction in St. Petersburg, Russia. Journal of Substance Abuse Treatment, 31:319-328.
Kushner et al. (Mar. 2002) Obesity pharmacology: past, present, and future, Current Opinion in Gastroenterology, pp. 213-220.
Landabaso et al. 1998. A randomized trial of adding fluoxetine to a naltrexone treatment programme for heroin addicts. Addiction, 93(5):739-744.
Le Bourdonnec et al. (2000) J. Med. Chem., 43:2489-2492.
Leppik (Dec. 2004) Zonisamide: chemistry, mechanism of action, and pharmacokinetics, Seizure, 13(Suppl 1):S5-9; discussion S10.
Leppik et al. (1993) Efficacy and safety of zonisamide: results of a multicenter study. Epilepsy Research; 14:165-173.
Lesch et al. 1991. Long-term fluoxetine treatment decreases 5-HT1A receptor responsivity in obsessive-compulsive disorder. Psychopharmacology, 105:415-420.
Lessig et al. (Dec. 2001) Topiramate for Reversing Atypical Antipsychotic Weight Gain, J. Am. Child Adolesc. Psychiatry 40(12):1364.
Levy et al. (Nov. 2002) Topiramate Produced Weight Loss Following Olanzapine-Induced Weight Gain in Schizophrenia, J. Clin. Psychiatry, 63(11):1045.
Levy et al. 1985. Utility of free level monitoring of antiepileptic drugs. Epilepsia, 26(3):199-205.
Lin et al. 2000. Development of high fat diet-induced obesity and leptin resistance in C57B1/6J mice. International Journal of Obesity, 24:639-646.
López-Ibor, Jr. et al. 1996. Double-blind comparison of fluoxetine versus clomipramine in the treatment of obsessive compulsive disorder. European Neuropsychopharmacology, 6:111-118.
Malcolm et al. (Jun. 1985) A Controlled Trial of Naltrexone in Obese Humans, International Journal of Obesity, 9:347-353.
Malhotra et al. (2002) Medical Management of Obesity Associated With Mental Disorders, Journal of Clinical Psychiatry, 63(suppl 4):24-32.
Matsuura (2000) Indication for Anterior Temporal Lobectomy in Patients with Temporal Lobe Epilepsy and Psychopathology, Epilepsia, 41(Suppl. 9):39-42.
McDougle et al. (Aug. 2000) A double-blind, placebo-controlled study of risperidone addition in serotonin reuptake inhibitor-refractory obsessive-compulsive disorder, Archive of General Psychiatry, 57(8):794-801.
McElroy et al. (2000) Pharmacologic agents for the treatment of acute bipolar mania, Biological Psychiatry, 48(6):539-557.
McElroy et al. (2004) Zonisamide in the Treatment of Binge-Eating Disorder: An Open-Label, Prospective Trial, J. Clin. Psychiatry, 65(1):50-56.
McElroy et al. (2004) Zonisamide is effective in the treatment of binge-eating disorder. Inpharma; 1428:10.
McLaughlin et al. (2003) The cannabinoid CB1 antagonists SR 141716A and AM 251 suppress food intake and food-reinforced behavior in a variety of tasks in rats. Behavioral Pharmacology; 14:583:588.
Michelson et al. (Nov. 2001) Atomexetine in the Treatment of Children and Adolescents with Attention Deficit/Hyperactivity Disorder: A Randomized, Placebo-Controlled, Dose-Response Study, Pediatrics,108(5):E83 Abstract.
Millet et al. 1999. Obsessive-compulsive disorder: Evaluation of clinical and biological circadian parameters during fluoxetine treatment. Psychopharmacology, 146:268-274.
Mitchell et al. (1987) High-Dose Naltrexone Therapy and Dietary Counseling for Obesity, Biological Psychiatry, 22:35-42.
Monteleone et al. 1995. Plasma melatonin and cortisol cirdadian patterns in patients with obsessive-compulsive disorder before and after fluoxetine treatment. Psychoneuroendocrinology, 20(7):763-770.
Morris, III (Dec. 3, 2000) the Effect of Zonisamide Administration on Patient Weight, A Scientific Exhibit at the American Epilepsy Society Annual Meeting, Los Angeles, California.
Must et al. (Oct. 27, 1999) The disease burden associated with overweight and obesity, JAMA, 282(16):1523-1529.
Najim et al., Dec. 1, 1993, Role of endorphins in benzodiazepine-induced hyperglycaemia in mice, Pharmacology Biochemistry and Behavior, 46(4):995-997.
Naltrexone (Oral Route), MayoClinic.com, 11 pp., 2009.
Nash et al., Jul. 1, 2004, Anxiety disorders, Medicine, 32(7):17-21.
NIH Publication No. May 3892, Dec. 2004, National Diabetes Statistics, 18 pp.
Navarro et al. (Jun. 2001) Topiramate for Clozapine-Induced Seizures, Am. J. Psychiatry, 158(6):968-969.
NDA 20-711, Approval Letter of Application No. NDA 20-711, Department of Health and Human Services, May 14, 1997, 3 pp.
NDA20-789, ZONEGRAN (zonisamide) Capsules 100 mg, FDA Approved Labeling Text, p. 1-24 (Mar. 27, 2000).
Neumeister et al. 1999. Addition of naltrexone to fluoxetine in the treatment of binge eating disorder. Am. J. Psychiatry, 156(5):797.
Ninan et al., 1992, An improved synthesis of noroxymorphont, Tetrahedron., 48(32):6709-6716.
Niswender et al. 1997. Effects of increased glucokinase gene copy number on glucose homeostatis and hepatic glucose metabolism. The Journal of Biological Chemistry, 272(36):22570-22575.
Note for guidance on stability testing of existing active substances and related finished product, Committee for Proprietary Medicinal Products (CPMP), Apr. 22, 1998, 9 pp.
Novi et al. (Apr.-Jun. 1990) The role of opioid antagonists in the treatment of obesity. Results of a clinical trial with naltrexone, Minerva Endocrinol. 15(2):121-3, Abstract.
O'Byrne et al., Jan. 1, 1990, Effects of drugs on glucose tolerance in non-insulin-dependent diabetes (part II), Drugs, Adis International Ltd., 40(2):204-219.
Okada et al. (1992) Effects of zonisamide on extracellular levels of monoamine and its metabolite, and on Ca2+ dependent dopamine release Epilepsy Research, 13:113-119.
Okada et al. (1995) Effects of zonisamide on dopaminergic system, Epilepsy Research, 22:198-205.
Olsen et al., (1990) Conjugate Addition Ligands of Opioid Antagonists. Methacrylate Esters and Ethers of 6Alpha- and 6Beta-Naltrexol, Journal of Medicinal Chemistry, American Chemical Society, 33(2):737-741.
Olszewski et al. (Jun. 13, 2001) Evidence of Interactions Between Melanocortin and Opioid Systems in Regulation of Feeding, Neuroreort, 12(8):1727-1730.
Oommen et al. (1999) Zonisamide: A new antiepileptic drug. Clinical Neuropharmacology, 22(4):192-200.
Ortho-Novum Tablets and Modicon Tablets Prescribing Information, Apr. 2002, 8 pp.
Otake et al. (May 15, 2005) Association of visceral fat accumulation and plasma adiponectin and colorectal ademona: evidence for participation of insulin resistance, Clinical Cancer Research 11:3642-3646.
Ovadia, Oct. 1999, A Novel Twist on Binge Eating Treatment, Psychiatric Dispatches in Primary Psychiatry; 6(10):24-29.
Paile-Hyvarinen et al., Mar. 14, 2003, Quality of life and metabolic status in mildly depressed women with type 2 diabetes treated with paroxetine: a single blind randomised placebo controlled trial, BMC Family Practive, Biomed Central, 4(1), 6 pp.

(56) References Cited

OTHER PUBLICATIONS

Paar et al., 2002, Bivalent ligands with rigid double-stranded DNA spacers reveal structural constraints on signaling by FcεRI, J. Immunol., 169:856-864.
Pasternak et al. (1980) Long-acting opiate agonists and antagonists: 14-hydroxydihydromorphinone hydrazones, Med. Chem, 23:674-676.
Pavuluri et al. (2002) Topiramate Plus Risperidone for Controlling Weight Gain and Symptoms in Preschool Mania, Journal of Child and Adolescent Psychopharmacology, 12(3):271-273.
Penn et al., 2003, Pharmacotherapy of obesity in the near term, Current Opinion in Endocrinology and Diabetes, 18(2):311-316.
Portoghese et al., 1982, Opioid agonist and antagonist bivalent ligands as receptor probes, Life Sciences, 31:1283-1286.
Portoghese et al., 1986, Synthesis and Opioid antagonist potencies of naltrexamine bivalent ligands with conformationally restricted spacers J. Med. Chem., 29:1650-1653.
Portoghese et al., 1986, Opioid agonist and antagonist bivalent ligands. The relationship between spacer length and selectivity at multiple opioid receptors, J. Med. Chem., 29:1855-1861.
Portoghese, 1992, The role of concepts in structure-activity relationship studies of opioid ligands, J. Med. Chem., 35:1927-1937.
Potter et al., 1997, Sustained Weight Loss Associated with 12-month topiramate Therapy, Epilepsia, Raven Press Ltd. New York, 38(Suppl 8):97.
Rao et al. (1998) Fixed-does combination therapy: panacea or poison?, Intensive Care Med, 24:283-285.
Reaven, G. M. 1995. Pathophysiology of insulin resistance in human disease. Physiological Reviews, 75(3):473-486.
Reents et al. (1988) Nalozone and naltrexone, Chest, 93(1):217-219.
Remington's Pharmaceutical Sciences. $18^{th}$ Edition; Easton, PA: Mack Publishing Co. (1990).
Reneric et al. (Nov. 1998) Opioid Receptor Antagonists in Psychiatry, CNS Drugs, 10(5):365-377.
Rezvani et al. 2000. Combination pharmacotherapy: A mixture of small doses of naltrexone, fluoxetine, and thyrotropin-releasing hormone analogue reduces alcohol intake in three strains of alcohol-preferring rats. Alcohol & Alcoholism, 35(1):76-83.
Romano et al. 2001. Long-term treatment of obsessive-compulsive disorder after an acute response: A comparison of fluoxetine versus placebo. Journal of Clinical Psychopharmacology, 21(1):46-52.
Rotzinger et al. (1999) Metabolism of some 'second' and 'fourth' generation antidepressants: iprindole, viloxazine, bupropion, mianserin, maprotiline, trazadone, nefazodone, and vaniafaxine, Cellular and Molecular Neurobiology, 19:430.
Rowland et al. (2001) Effects of the cannabinoid receptor antagonist SR 141716, alone and in combination with dexfenfluramine or naloxone, on food intake in rats. Psychopharmacology; 159:111-116.
Saba et al. 2002. Lamotrigine-clozapine combination in refractory schizophrenia: Three cases. The Journal of Neuropsychiatry and Clinical Neurosciences, 14(1):86.
Sackellares et al. (1985) Pilot study of zonisamide (1,2-benzisoxazole-3-methanesulfonamide) in patients with refractory partial seizures. Epilepsia, 26(3):206-211.
Saper et al. (2002) The need to feed: Homeostatic and hedonic control of eating, Neuron, 36:199-211.
Sashiwa et al., 2000, Chemical modification of chitosan. 3. Hyperbranched chitosan-sialic acid dendrimer hybrid with tetraethylene glycol spacer, Macromolecules, 33:6913-6915.
Sayre et al., 1984, Design and synthesis of naltrexone-derived affinity labels with nonequilibrium opioid agonist and antagonist activities. Evidence for the existence of different receptor subtypes in different tissues, J. Med. Chem., 27:1325-1335.
Scheen et al., May 1, 2005, Diabete sucre iatrogene: l'exemple des anti-phsychogiques atypiques, Revue Medicale de Liege, 60(5-6):455-460.
Schmidhammer et al. (1994) Mixed Azines of Naloxone with Dihydromorphinone Derivatives. A. Helv. Chim. Acta; 77:999.
Schmidt et al. (1993) Zonisamide for add-on treatment of refractory partial epilepsy: a European double-blind trial. Epilepsy Research; 15:67-73.
Schimmel et al., 1974, Inhibition by diphenylhydantoin of the diabetogenic action of streptozocin, Horm. Metab. Res. 6:475-477.
Shapira et al. (2000) Treatment of Binge-Eating Disorder with Topiramate: A Clinical Case Series. J. Clin. Psychiatry; 61(5):368-371.
Shapira et al. 2004. A double-blind, placebo-controlled trial of olanzapine addition in fluoxetine-refractory obsessive-compulsive disorder. Biol. Psychiatry, 550:553-555.
Shapiro et al. (2005) Additive Benefits of Combination Therapy with Sibutramine and Rimonabant on Body Weight, Insulin Sensitivity and Lipoproteins in Diet-Induced Obese Mice, 2005 NAASO Annual Meeting, Poster 405-P.
Shelton (2003) Classification of Antidepressants and their Clinical Implications, Primary Care Companion J. Clin. Psychiatry, 5(Supp. 7):27-32.
Shriqui et al. (Jul. 2002) Atypical Antipsychotics, The Canadian Journal of CME, pp. 65-80.
Sitsen et al., 2001, Drug-drug interaction studies with mirtazapine and carbamazepine in healthy male subjects, European Journal of Drug Metabolism and Pharmacokinetics, 26(1-2):109-121.
Sneer et al., Protective effect of diphenylhydantoin on the diabetes-inducing effect of alioxan, database accession No. 1980:34024.
Spigset et al. (2001) Therapeutic Approaches to Bulimia Nervosa, Expert Opinion on Therapeutic Patents, 11(3):463-477.
Srivastava et al. 1975. Organic disulfides and related substances. 38. Some disulfide and trisulfide sulfinate salts as antiradiation drugs. Journal of Medicinal Chemistry, 18(8):798-802.
Steffen et al. 2006. Emerging drugs for eating disorder treatment. Expert Opin. Emerging Drugs, 11(2):315-336.
Stein (Feb. 15, 2000) Neurobiology of the obsessive-compulsive spectrum disorders, Biological Psychiatry 47(4):296-304.
Stein (Aug. 3, 2002) Obsessive-compulsive disorder, Lancet 360(9330):397-405.
Stepinski et al. (1991) Internat. J. of Peptide & Protein Res., 38:588-592.
Storch et al. 2006. Clinical predictors of early fluoxetine treatment response in obsessive-compulsive disorder. Depression and Anxiety, 23:429-433.
Stromberg et al. (2002) A comparison of the effects of 6-beta naltrexol and naltrexone on the consumption of ethanol or sucrose using a limited-access procedure in rats. Pharmacology, Biochemistry, and Behavior, 72:483-490.
Swedo et al. 1998. Pediatric autoimmune neuropsychiatric disorders associated with streptococcal infections: Clinical description of the first 50 cases. Am. J. Psychiatry, 155(2):264-271.
Symons et al. 2004. Self-injurious behavior and the efficacy of naltrexone treatment: A quantitative synthesis. Mental Retardation and Developmental Disabilities Research Reviews, 10:193-200.
Tamiz et al., 2000, Application of the bivalent ligand approach to the design of novel dimeric serotonin reuptake inhibitors, J. Am. Chem. Soc., 122:5393-5394.
Tamiz et al., 2001, Pharmacological and behavioral analysis of the effects of some bivalent ligand-based monoamine reuptake inhibitors, J. Med. Chem., 44:1615-1622.
Testa, 2004, Prodrug research: futile or fertile?, Biochemical Pharmacology, 68:2097-2106.
Thearle et al. (2003) Obesity and Pharmacology, Endocrinology and Metabolism Clinics of North American, W.B. Suanders Company, Philadelphia US 32(4):1005-1024.
Thombre et al. (2004) Osmotic drug delivery using swellable-core technology, Journal of Controlled Release 94:75-89.
Tollefson et al. (1997) Olanzine versus haloperidol in the treatment of schizophrenia and schizoaffective and schizophreniform disorders: results of an international collaborative trial, Am J. Psychiatry, 154(5):457-465.
Tutka et al., 2004, Convulsant and anticonvulsant effects of bupropion in mice, European Journal of Pharmacology, 499:117-120.
Van Schaftingen et al. (1992) The regulatory protein of liver glucokinase. Advan. Enzyme Regul., 32:133-148.

(56) References Cited

OTHER PUBLICATIONS

Vieta et al. (2003) 1-year follow-up of patients treated with risperidone and topiramate for a manic episode, J Clin Psychiatry, 64(7):834-829.
Vieta et al. (2004) Effects on weight and outcome of long-term olanzapine-topiramate combination treatment in bipolar disorder. Journal of Clinical Psychopharmacology 24(4):374-378.
Vythilingum et al. 2005. Obsessive-compulsive disorders and dermatologic disease. Dermatologic Clinics, 23:675-680.
Wadden et al. (2000) Effects of Sibutramine Plus Orlistat in Obese Women Following 1 Year of Treatment by Sibutramine Alone: A Placebo-Controlled Trial, Obesity Research; 8(6):431.
Walker et al. (1988) Chronic Toxicity of the Anticonvulsant Zonisamide in Beagle Dogs, Fundamental and Applied Toxicology 11:333-342.
Wang et al. (2002) Gabapentin augmentation therapy in bipolar depression, Bipolar Disorders 4:296-301.
Weintraub et al. (1992) Long-term Weight Control Study I (weeks 0 to 34) 'The Enhancement of Behavior Modification, Caloric Restriction, and Exercise by Fenfluramine Plus Phentermine versus Placebo', Clinical Pharmacology & Therapeutics, 51(5):586-94.
Welty et al. (Nov. 30-Dec. 5, 2001) Weight Loss Associated With Use of Zonisamide in European and US Clinical Trials, A Compendium of Posters and Platform Sessions for Zonegran®, Presented at the Annual Meeting 2001 of the American Epilepsy Society, Philadelphia, Pennsylvania.
Wermuth, Apr. 2006, Similarity in drugs: reflections on analogue design, Drug Discovery Today, 11(7/8):348-354.
Werneke et al. (2002) Options for Pharmacological Management of Obesity in patients Treated with Atypical Antipsychotics, International Clinical Psychopharmacology, 17(4):145-160.
Wheatley et al., 1998, Mirtazapine: efficacy and tolerability in comparison with fluoxetine in patients with moderate to severe major depressive disorder, J. Clin Psychiatry, 59(6):306-312, Abstract.
White et al. 2002. Development and validation of the food-craving inventory. Obesity Research, 10(2):107-114.
Wilding (2004) Clinical evaluation of anti-obesity drugs. Current Drug Targets; 5:325-332.
Willmore, L. J. 2004. Commentary on Leppik. Seizure, 13S:S10.
Wilner, 2002, Is Weight Loss With Zonisamide Gender-Specific?, Annual Meeting of the American Epilepsy Society, https://secure.neurohub.net/cgi-perl/get.cgi?pub=52318&ext=htm, 1 pp.
Wolff (1995) Burger's Medicinal Chemistry and Drug Discovery, John Wiley & Sons, 5th Ed. 1:975-977.
Yeomans et al. (2002) Opioid peptides and the control of human ingestive behaviour, Neuroscience and Biobehavioral Reviews, 26:712-728.
Yoshimasu et al. (2003) Psychotropic Drug-Induced Obesity, Nippon Rinsho, 61(Suppl. 6):825-829. (English translation of Japanese Office Action containing Examiner's characterization of reference is appended to reference: Notice of Reasons for Rejection, Application No. 2006-549530).
Yu et al. (2005) Influence of insulin treatment on insulin sensitivity in insulin requiring type 2 diabetes patents, Diabetes Research and Clinical Practice, 68S1:S54-S59.
Zeng et al., 1988, Convenient synthesis of 9-alkyl and 9-arylacridines from [2-(trimethylsilyl)ethoxy]methyl (sem) protected acridone, Tetrahedron Letters, 29(40):5123-5124.
Zhang et al. (1994) Positional Cloning of the Mouse obese gen and its humane homologue, Nature, 372:425-432.
Zhu et al. (Apr. 3, 2002) Pharmacologic Treatment of Easting Disorders, Canadian Journal of Psychiatry, 47(3):227-234.
Zitterl et al. 1999. Efficacy of fluoxetine in Austrian patients with obsessive-compulsive disorder. Wiener Klinische Wochenschrift, 111(11):439-442.
Zohar et al. 1987. Serotonergic responsivity in obsessive-compulsive disorder. Arch. Gen. Psychiatry, 44:946-951.
Zonegran.TM. (zonisamide) capsules, FDA Approved Labeling Text, Mar. 27, 2000, 24 pp.
Zonisamide (Oral Route), MayoClinic.com, 12 pp., 2009.
International Search Report and Written Opinion, date of mailing Mar. 10, 2011 in 14 pages.
Albaugh et al., 2005, Topiramate prevents the rapid weight gain and adiposity in a model of atypical antipsychotic drug-induced obesity, Fed. of American Soc. For Experimental Biology, 19(5, Suppl. S, Part 2):A1130.
Bays et al., Aug. 1, 2007, Adiposopathy: treating pathogenic adipose tissue to reduce cardiovascular disease risk, Current Treatment Options in Cardiovascular Medicine, 9(4):259-271.
Chen et al., 2005, Combination treatment of clozapine and toperamate in resistant rapid-cycling bipolar disorder, Clin. Neuropharmacol. 28(3):136-138.
Chen et al., Jun. 2003, Nonketotic hyperosmolar syndrome from olanzapine, lithium, and valproic acid cotreatment, Annals of Pharmacotherapy, 37(6):919-920.
Cuparencu et al., 1993, Effects of some benzodiazepines on glycemia in albino rats, Romanian Journal of Physiology, 30(1-2):7-15 (abstract).
Durgin et al., 2005, Pharmaceutical Practice for Technicians, 3rd Edition, Thomson Delmar Learning, p. 174.
Greenway et al., Dec. 2009, Comparison of combined bupropion and naltrexone therapy for obesity with monotherapy and placebo, J. Clin Endocrinol Metab, 94(12):4898-4906.
Greenway et al., Jan. 2009, Rational design of a combination medication for the treatment of obesity, Obesity, 17(1):30-39.
Greenway et al., Jun. 2006, Bupropion and naltrexone for the treatment of obesity, Diabetes: Abstract Book: 66th Scientific Sessions, 55(Supplement 1):A394.
Greenway et al., Jun. 2006, Bupropion and naltrexone for the treatment of obesity, poster, 1 pg.
Hagan et al., Dec. 1997, Combined nalozone and flouxetine on deprivation-induced binge eating of palatable foods in rats, Pharmacol Biochem Behav, 58(4):1103-1107.
Halpern et al., Jul. 27, 2010, Combinations of drugs in the tratment of obesity, Pharmaceuticals, 3:2398-2415.
Janssen et al., 1999, Effects of sex on the change in visceral, subcutaneous adipose tissue and skeletal muscle in response to wieght loss, International Journal of Obesity, 23, pp. 1035-1046.
Jones et al., 2003, Effect of naltrexone on food intake and body weight in Syrian hamsters depends on metabolic status, Physiology & Behavior 28:67-72.
Kelly et al., 2006, Adjunct divalproex or lithium to clozapine in treatment-resistant schizophrenia, Psychiatric Quarterly, 77(1):81-94.
Kristeller et al., Jan. 12, 1999, An exploratory study of a meditation-based intervention for binge eating disorder, J. Health Psychol, 4(3):357-363.
Kuk et al., 2006, Visceral fat is an independent predictor of all-cause mortality in men, Obesity, 14(2):336-341.
Lowry, Feb. 2008, Study: bupropion-naltrexone combo best for weight loss, Clinical Psychiatric News, 1 pp.
National Institutes of Health, Apr. 18, 2008, Efficacy and safety study of combination therapy to treat uncomplicated obesity, http://clinicaltrials.gov/show/NCT00364871, 5 pp.
NDA 20-789/S-005 ZONEGRAN (zonisamide) Capsules 100 mg, FDA Approved Labeling Text dated Oct. 7, 2002, 2 pp.
Tavakoli et al., Jul. 2003, Diabetic ketoacidosis in a patient with olanzapine, valproic acid, and venlafaxine, Southern Medical Journal, 96(7):729-730.
Turnbull et al., Jan. 1985, The effect of valproate on blood metabolite concentrations in spontaneously diabetic, ketoacidotic, bb/e wistar rats, Diabetes Research 2(1):45-48.
Wadden et al., Jan. 2011, Weight loss with naltrexone SR/bupropion SR combination therapy as an adjunct to behavior modification: the COR-BMOD trial, Obesity, 19(1):110-120.
Wieczorek et al., 2001, The effects of the selective serotonin reuptake-inhibitor fluvoxamine on body weight in Zucker rats are mediated by cortocotrophin-releasing hormone, International Journal of Obesity, 25(10):1566-1569.
Wilcox et al., 2009, An open-label study of naltrexone and bupropion combination therapy for smoking cessation in overweight and obese subjects, Addictive Behaviors, 35(3):229-234.

(56) References Cited

OTHER PUBLICATIONS

ClinicalTrials.gov archive, Apr. 21, 2008, A phase 3 study comparing the safety and efficacy of naltrexone SR/bupropion SR and placebo in obese subjects with type 2 diabetes mellitus, 3 pp.
Cunningham, "Diethylpropion in the treatment of obesity," The Journal of the College of General Practitioner, May 1963, 6(2):347-349.
Fujioka et al., "Contribution of intra-abdominal fat accumulation to the impairment of glucose and lipid metabolism in human obesity," Metabolism, Jan. 1987, 36(1):54-59.
Kivimäki et al., "Common mental disorder and obesity-insight from four repeat measures over 19 years: prospective Whitehall II cohort study," BMJ 2009: 339:b3765 doi 10.1136/bmj.b3765.
Gormally et al., "The assessment of binge eating severity among obese persons," Addictive Behaviors, 1982, 7(1):47-55.
McLaughlin et al., "Nalmefene decreases meal size, food and water intake and weight gain in Zucker rats," Pharmacology Biochemistry and Behavior, 1983, 19(2):235-240 (abstract).
Pandit, Introduction to the Pharmaceutical Sciences, 2007, p. 154 (Lippincott Williams & Wilkins, Baltimore, MD).
Shuman et al., "Abnormal body fat distribution detected by computed tomography in diabetic men," Investigative Radiology, Jun. 1986, 21(6):483-487.
Stansfeld et al., "Social class and minor psychiatric disorder in British Civil Servants: a validated screening survey using the General Health Questionnaire," Psychol. Med. 1992, 22(3):739-749.
Adis Data Information BV, 2010, Naltrexone/Bupropion Contrave ®; Naltrexone SR/Bupropion SR, Adis R&D Profile, 10(1):25-32.
Alger et al., Apr. 1991, Effect of a tricyclic antidepressant and opiate antagonist on binge-eating behavior in normoweight bulimic and obese, binge-eating subjects, The American Journal of Clinical Nutrition, 53(4):865-871.
Campana et al., Jan. 2005, P.6.034 Naltrexone and cravings: does it work with eating disorders?, European Neuropsychopharmacology, 15:S283.
Carter et al. 2003. Pharmacologic treatment of binge-eating disorder, The International Journal of Eating Disorders, 34(Suppl):S74-S88.
Casado et al., Apr. 2003, Sibutramine decreases body weight gain and increases energy expenditure in obese Zucker rats without changes in NPY and orexins, Nutr Neurosci, 6(2):103-111 (abstract).
ClinicalTrials.gov archive, May 2012, Cardiovascular outcomes study of Naltrexone SR/Bupropion SR in overweight and obese subjects with cardiovascular risk factors (the light study), 4 pp.
Eckel et al., Apr. 16, 2005, The metabolic syndrome, The Lancet 365:1415-1428.
Greenway et al., Oct. 22, 2010, Effect of naltrexone plus bupropion on weight loss in overweight and obese adults (COR-I): a multicentre, randomized, double-blind, placebo-controlled, phase 3 trial, Lancet, 376:595-605.
Hausenloy, 2009, Contrave™: Novel treatment for obesity, Clinical Lipidology, 4(3):279-285.
Horne et al., Jul. 1988, Treatment of bulimia with bupropion: a multicenter controlled trial, The Journal of Clinical Psychiatry, 49(7):262-266.
Johnson et al., Oct. 14, 2010, Food effects on the pharmacokinetics of morphine sulfate and naltrexone hydrochloride extended release capsules, Advances in Therapy, 27(11):846-858.
Jonas et al., 1986, Treatment of binge-eating an open-study of naltrexone, Society for Neuroscience Abstracts, 12(1):595.
Kennett et al., Nov. 2010, New approaches to the pharmacological treatment of obesity: can they break through the efficacy barrier?, Pharmacology Biochemistry and Behavior, 97(1):63-83.
Khaylis et al., Nov. 2010, A review of efficacious technology-based weight-loss interventions: five key components, Telemedicine and e-Health, 16(9):931-938.
Klein et al., Jun. 1, 2009, Naltrexone plus bupropion combination causes significant weight loss without worsening psychiatric symptoms, Diabetes, 58(Suppl. 1): p. A444, Abstract 1739-P.
Ludman et al., "Does depression reduce the effectiveness of behavioral weight loss treatment?" Behav Med. 2010; 35(4):126-134, Abstract only.

Luppino et al., Mar. 2010, Overweight, obesity, and depression: a systematic review and meta-analysis of longitudinal studies, Arch Gen Psychiatry, 67(3):220-229.
Marrazzi et al., Feb. 1995, Binge eating disorder: response to naltrexone, International Journal of Obesity, 19(2):143-145.
McElroy et al., Jun. 1, 2010, An open-label study evaluating the naltrexone SR/bupropion SR combination therapy in overweight or obese subjects with major depression, Diabetes, 59(Suppl. 1):A483.
Meyer, Dec. 2008, Alleviation of both binge eating and sexual dysfunction with naltrexone, Journal of Clinical Psychopharmacology, 28(6):722-723.
Midha et al., May 2005, Exposure measures applied to the bioequivalence of two sustained release formulations of bupropion, International Journal of Clinical Pharmacology and Therapeutics, 43(5):244-254.
Pagoto et al., Association of Major Depression and Binge Eating Disorder with Weight Loss in a Clinical Setting, Obesity, Nov. 2007; 15(11):2557-2559.
Plodkowski et al., 2009, Bupropion and naltrexone: a review of their use individually and in combination for the treatment of obesity, Expert Opin. Pharmacother. 10(6):1069-1081.
Van Gaal et al., Aug. 1998, Sibutramine and fat distribution: is there a role for pharmacotherapy in abdominal/visceral fat reduction?, Int J Obes Relat Metab Disord, Suppl 1:S38-40; discussion S41-2 (abstract).
A multicenter, randomized, double-blind, placebo-controlled study assessing the occurrence of major adverse cardiovascular events (MACE) in overweight and obese subjects with cardiovascular risk factors receiving naltrexone SR/bupropion SR, Adis Clinical Trials Insight (Nov. 15, 2011), 5 pp.
Altomonte et al., 1988, Effect of fenfluramine on insulin/growth hormone ratio in obese subjects, Pharmacology, 36(2):106-111.
Bakris et al., 2002, Orlistat improves blood pressure and control in obese subjects with treated but inadequately controlled hypertension, Journal of Hypertension, 20(11):2257-2267.
Bengtsson, 1993, The consequences of growth hormone deficiency in adults, Acta Endocrinol. (Copenh.), 128(Suppl 2):2-5.
Brown et al., 2012, Current and emerging directions in the treatment of eating disorders, Substance Abuse: Research and Treatment, 6:33-61.
Brunk, Sep. 1, 2009, Significant weight loss shown with naltrexone/bupropion combo, Thoracic Surgery News, http://www.thoracicsurgerynews.com/?id=95937&tx_ttnews[tt_news]=86987&cHash=a97b7f3c0f6a8c6a3b3ca96df9a6b73f, 1 pp.
Carson et al., May 1996, Pilot study of the use of naltrexone to treat the severe pruritis of cholestatic liver disease, Amer. J. Gastroenterology, 91(5):1022-1023.
Chakraborty et al., 2010, Management of anorexia and bulimia nervosa: an evidence-based review, Indian J Psychiatry, 52:174-186.
Cleveland Clinic Press Release: "Clinical Trial Testing Safety of Obesity Drug Contrave Halted; 50 Percent Interim Data Released by the Study's Executive Committee", May 12, 2015, retrieved from http://my.clevelandclinic.org/about-cleveland-clinic/newsroom/releases-videos-newsletters/2015-5-12-clinical-trial-testing-safety-of-obesity-drug-contrave-halted.
Clinical Trials.gov, A Multicenter, randomized, double-blind, placebo-controlled study assessing the occurrence of major adverse cardiovascular events (MACE) such as cardiovascular death, non-fatal myocardial infarction, and non-fatal stroke in overweight and obese subjects who are at a higher risk of having these events because they ahv diabetes and/or other cardiovascular risk factors, NTC01601704, May 7, 2013, 4 pp.
Clinical Trials.gov, Jul. 13, 2009, An open-label study assessing the safety and efficacy of naltrexone sustained release (SR)/bupropion sustained release (SR) in overweight or obese subjects with major depression, 2 pp.
ClinicalTrials.gov, Apr. 3, 2007, A safety and efficacy study of naltrexone sr/bupropion sr and placebo in overweight and obese subjects participating in an intensive behavior modification program, NCT00456521, 5 pp.
Das et al., 2003, Controlled-release of oral dosage forms, Formulation, Fill & Finish, pp. 10-16.

(56) References Cited

OTHER PUBLICATIONS

De Boer et al., 1995, Clinical aspects of growth hormone deficiency in adults, Endocrine Reviews, 16(1):63-86.
Eid et al., 2005, Effective treatment of polycystic ovarian syndrome with roux-en-y gastric bypass, Surgery for Obesity and Related Diseases, 1:77-80.
Ghisoli et al., 1980, Effects of dopaminergic receptor stimulation and opioid receptor blockade on GH incretion: preliminary findings, Boll. Soc. Ital. Biol. Sper., 56(12):1222-1225.
Glod et al., Jul.-Sep. 2003, Open trial of bupropion sr in adolescent major depression, J Child Adolesc Psychiatr Nurs, 16(3):123-130.
Goodman & Gillman's, The Pharmacological Basis of Therapeutics, 10th Ed., Edited by J. Hardman and L. Limbird, 2001, p. 6.
Gudmundur et al., 1997, Growth hormone treatment of abdominally obese men reduces abdominal fat mass, improves glucose and lipoprotein metabolism, and reduces diastolic blood pressure, J. Clin. Endocrin. and Metab., 82(3):727-734.
Guidance for Industry Estimating the Maximum Safe Starting Dose in Initial Clinical Trials for Therapeutics in Adult Healthy Volunteers, U.S. Department of Health and Human Services, U.S. Food and Drug Administration Center for Drug Evaluation and Research (CDER), Pharmacology and Toxicology, Jul. 2005.
Halford et al., May 2010, Pharmacological management of appetite expression in obesity, Nature Reviews Endocrinology, 6(5):255-269.
Herper, "A Top Cardiologist Says A Diet Drug Maker Misled Patients and Investors", Forbes, May 12, 2015, retrieved from http://www.forbes.com/sites/matthewherper/2015/05/12/a-top-cardiologist-says-a-diet-drug-maker-misled-patients-and-investors/#.
Herper, "Heart Benefit for Orexigen Drug Nearly Vanishes with New Data", Forbes, May 12, 2015, retrived from http://www.forbes.com/sites/matthewherper/2015/05/12/heart-benefit-for-orexigen-drug-nearly-vanishes-with-new-data/.
Herper, Mar. 5, 2015, Top FDA Official Says Orexigen Study Result 'Unreliable,' Misleading, http://www/forbes.com/sites/matthewherper/, 4 pp.
Hollander et al., Oct. 21, 2013, Effects of naltrexone sustained-release/bupropion sustained release combination therapy on body weight and glycemic parameters in overweight and obese patients with type 2 diabetes, Diabetes Care, 36(12):4022-4029.
Husten, Mar. 3, 2015, Orexigen Released Interim Data Without Approval of Trial Leaders, http://ww/forbes.com/sites/harryhusten, 6 pp.
Ioannides-Demos et al., 2005, Pharmacotherapy for obesity, Drugs, 65(10):1391-1418.
Johnston et al., 2002, Pharmacokinetic optimization of sustained-release bupropion for smoking cessation, Drugs, 62(Suppl. 2):11-24.
Kruger, 2000, Psychotherapy of anorexia nervosa, bulimia nervosa and binge-eating disorder, J. Psychiatry Neurosci, 25(5):497-508.
Laessle et al., May 1997, A comparison of resting metabolic rate, self-rated food intake, growth hormone, and insulin levels in obese and nonobese preadolescents, Physiol. Behav., 61(5):725-729.
McElroy et al., Jun. 2013, Naltrexone/bupropion combination therapy in overweight or obese patients with major depressive disorder: results of a pilot study, Prim Care Companion CNS Disord, 15(3), 17 pp.
McElroy et al., May 7, 2012, Pharmacological management of binge-eating disorder: current and emerging treatment options, Therapeutics and Clinical Risk Management, 8:219-241.
Meyer et al., Sep. 1984, Bioequivalence, dose-proportionality, and pharmacokinetics of naltrexone after oral administration, J. Clin. Psychiatry, 45(9)(Sec. 2):15-19.
Milano et al., May-Jun. 2005, Treatment of bulimia nervosa with fluvoxamine: a randomized controlled trial, Advances in Therapy, 22(3):278-283.
Miyazaki, 2005, Adiposity and Drug Treatment, Resident Notes, 7(4):499-502.

Mukherjee, "UPDATE: Takeda threatens to break off Orexigen collab after Contrave data drama", BioPharmaDive, May 13, 2015, retrieved from http://www.biopharmadive.com/news/update-takeda-threatens-to-break-off-orexigen-collab-after-contrave-data-d/396940/.
Oncken et al., 2001, Adverse effects of Oral naltrexone: an analysis of data from two clinical trials, Psychopharmacology, 154:397-402.
Orexigen Therapeutics Press Release: "Orexigen Therapeutics Provides Statement on Termination of the Light Study and Updates on Contrave Collaboration with Takeda Pharmaceuticals", May 12, 2015, retrieved from http://ir.orexigen.com/phoenix.zhtml?c=207034&p=irol-newsArticle_Print&ID=2047312.
Orexigen Therapeutics Press Release: "Takeda Pharmaceuticals and Orexigen Therapeutics Announce Termination of the Cardiovascular Outcomes Study (Light Study) of the Obesity Drug Contrave® (naltrexone HCl and bupropion HCl)", May 12, 2015, retrieved from http://ir.orexigen.com/phoenix.zhtml?c=207034&p=irol-newsArticle_Print&ID=2046959.
Orexigen Therapeutics, Inc., 2008, A safety and efficacy study comparing naltrexone SR/bupropion SR and placebo in obese type 2 diabetics, http://clinicaltrials.gov/ct2/show/NCT00474630, 3 pp.
Orexigen Therapeutics, Inc., Method-of-use study assessing the effect of naltrexone sustained release (SR)/bupropion SR on body weight and cardiovascular risk factors in overweight and obese subjects, http://clinicaltrials.gov/ct2/show/NCT01764386, 5 pp. Feb. 9, 2013.
Patel et al., Jun. 2011, A hospital-based observational study of type 2 diabetic subjects from Gujarat, India, Journal of Health, Population and Nutrition, 29(3):265-272.
Pearlstein et al., 2003, A double-blind, placebo-controlled trial of fluvoxamine in binge eating disorder; a high placebo response, Arch Womens Ment Health, 6:147-151.
Ramlo-Halsted et al., 2000, The natural history of type 2 diabetes: practical points to consider in developing prevention and treatment strategies, Clin. Diabetes, 18(2).
Rao, Mar. 2001, Insulin resistance syndrome, American Family Physician, 63(6):1159-1163.
Remington's Pharmaceutical Sciences, 1980, 16th ed., Mack Publishing Company, Arthur Osol. Editor, pp. 1553-1584.
Remington's Pharmaceutical Sciences, 1980, 16th ed., Mack Publishing Company, Arthur Osol. Editor, pp. 1594-1613.
Ricca et al., 2001, Fluoxetine and fluvoxamine combined with individual cognitive-behavior therapy in binge-eating disorder: a one-year follow-up study, Psychotherapy and Psychosomatics, 70:298-306.
Richelsen et al., Feb. 1994, Growth hormone treatment of obese women for 5 wk: effect on body composition and adipose tissue LPL activity, Am J. Physiol., 266(2 Pt 1):11-16.
Stedman's Medical Dictionary, 28th ed., Lippincott Williams & Wilkins, Philadelphia, 1999, pp. 490-491 and 1552.
Tallarida et al., 1996, Testing for synergism over a range of fixed ratio drug combinations: replacing the isobologram, Life Sciences, 58(2):PL23-PL28.
Tallarida, 2001, Drug synergism: its detection and applications, J. Pharmacol. and Expt. Therap., 298(3):865-872.
Wellbutrin® (bupropion hydrochloride) tablets, in Physicians' Desk Reference, 49th edition, 1995, pp. 824-827, 150.
White et al., 2003, Clarifying the role of insulin in type 2 diabetes management, Clinical Diabetes, 21(1):14-21.
Wong et al., Aug. 2004, Starting insulin treatment in type 2 diabetes, Australian Prescriber, 27(4):93-96.
IPRP dated Jul. 26, 2012 in PCT/US11/20712.

* cited by examiner

METHODS OF PROVIDING WEIGHT LOSS THERAPY IN PATIENTS WITH MAJOR DEPRESSION

BACKGROUND OF THE INVENTION

1. Field of the Invention

The present invention relates to methods of providing weight loss therapy, particularly for patients suffering from major depression.

2. Description of the Related Art

Obesity has been defined in terms of body mass index (BMI). BMI is calculated as weight (kg)/[height (m)]$^2$. According to the guidelines of the U.S. Centers for Disease Control and Prevention (CDC) and the World Health Organization (WHO), for adults over 20 years old, BMI falls into one of the following categories: below 18.5 is considered underweight, 18.5-24.9 is considered normal, 25.0-29.9 is considered overweight, and 30.0 and above is considered obese (World Health Organization. Physical status: The use and interpretation of anthropometry. Geneva, Switzerland: World Health Organization 1995. WHO Technical Report Series).

The diagnosis of mental disorders is typically based on the criteria provided in the Diagnostic and Statistical Manual of Mental Disorders, fourth edition (DSM-IV) (American Psychiatric Association; Diagnostic and Statistical Manual of Mental Disorders, fourth edition (DSM-IV), Washington, D.C., American Psychiatric Press, 1994). Three major categories of depression described in the DSM-IV are major depressive disorder (i.e., unipolar major depression), dysthymic disorder (i.e., dysthymia), and bipolar disorder (i.e., manic-depressive illness). There are also several subtypes of these main categories of depression. For example, atypical depression is a subtype of all three main types of depression that is characterized by the capacity to be cheered up when presented with positive events (see id.).

According to the DSM-IV, the essential feature of major depressive disorder is a period of at least two weeks during which an individual experiences a depressed mood or the loss of interest or pleasure in nearly all activities (see id). A diagnosis of major depressive disorder also requires at least four additional symptoms that may include changes in appetite or weight; insomnia; psychomotor agitation or retardation; decreased energy level; feelings of worthlessness or guilt; difficulty thinking, concentrating, or making decisions; and recurrent thoughts of death, suicidal ideation, or attempts to commit suicide (see id).

In contrast, dysthymic disorder is a milder form of depression with symptoms similar to, but less severe than, those of major depressive disorder. Bipolar disorder is characterized by extreme swings in mood between mania and depression, with mania being accompanied by euphoria, grandiosity, increased energy, decreased need for sleep, rapid speech, and risk taking (see id).

Depression has been linked to obesity, with recent studies identifying a specific link between major depression (i.e., major depressive disorder) and overweight or obesity. Depression has also been linked to emotional eating, which in turn is linked to high BMI. Further, depressed patients are known to exhibit weight gain as a side effect of certain depression therapies.

U.S. Pat. Nos. 7,375,111 and 7,462,626 disclose the combination of naltrexone and bupropion for weight loss therapy. Further, U.S. Pat. No. 5,817,665 discloses examples in which the combination of naltrexone and an antidepressant is used to treat depression in individuals who are also obese or crave sweets. However, a need exists for an effective method for the treatment of overweight or obesity in the difficult to treat population of overweight or obese patients suffering from major depression. A need also exists for an effective method to concurrently treat major depression and overweight or obesity.

SUMMARY OF THE INVENTION

Disclosed herein are methods of providing weight loss therapy, particularly for patients suffering from major depression. In some embodiments, the methods unexpectedly provide the same amount of weight loss in, overweight or obese patients who are suffering from major depression as in overweight or obese patients who are not suffering from major depression. In some embodiments, the dosages of naltrexone and bupropion unexpectedly treat both overweight or obesity and major depression.

In some embodiments, a method for providing weight loss therapy to a patient is provided, comprising: identifying a patient suffering from major depressive disorder, where the patient is also overweight or obese; and reducing weight of the patient by administering to the patient naltrexone or a pharmaceutically acceptable salt thereof and bupropion or a pharmaceutically acceptable salt thereof, where the naltrexone or pharmaceutically acceptable salt thereof is in an amount effective to enhance the weight loss activity of the bupropion or pharmaceutically acceptable salt thereof. In certain embodiments, the method further comprises reducing symptoms of depression in the patient. In certain embodiments, the patient has been diagnosed as suffering from major depressive disorder using the Montgomery-Åsberg Depression Rating Scale. In certain embodiments, the patient has been diagnosed as suffering from major depressive disorder using the Inventory of Depressive Symptomatology. In certain embodiments, the patient is not suffering from bipolar disorder. In certain embodiments, the patient has a body mass index of 25 kg/m$^2$ or above. In certain embodiments, the patient has a body mass index of 30 kg/m$^2$ or above. In certain embodiments, the patient is overweight. In certain embodiments, the patient is obese. In certain embodiments, the patient is female. In certain embodiments, the weight-loss inducing combination is administered at least once per day. In certain embodiments, the weight-loss inducing combination is administered more than once per day. In certain embodiments, the weight-loss inducing combination is administered for a period of at least 12 weeks. In certain embodiments, the weight-loss inducing combination is administered for a period of at least 24 weeks. In certain embodiments, the naltrexone or pharmaceutically acceptable salt thereof is administered prior to or subsequent to the bupropion or pharmaceutically acceptable salt thereof. In certain embodiments, the naltrexone or pharmaceutically acceptable salt thereof and the bupropion or pharmaceutically acceptable salt thereof are in a single oral dosage form. In certain embodiments, the single oral dosage form further comprises a pharmaceutically acceptable excipient, diluent, or carrier. In certain embodiments, the amount of naltrexone or pharmaceutically acceptable salt thereof is about 5 mg to about 50 mg per day. In certain embodiments, the amount of bupropion or pharmaceutically acceptable salt thereof is about 30 mg to about 500 mg per day. In certain embodiments, the amount of the naltrexone or pharmaceutically acceptable salt thereof is about 5 mg to about 50 mg per day; and the amount of the bupropion or pharmaceutically acceptable salt thereof is about 30 mg to about 500 mg per day. In certain embodiments, the amount of the naltrexone or pharmaceutically acceptable salt thereof is about 4 mg to about 50 mg per day; and the amount of the bupropion or pharmaceutically acceptable salt thereof is about 30 mg to about 500 mg per day. In certain embodiments, the amount of naltrexone or pharmaceutically acceptable salt thereof is about 16 mg or about 32 mg per day; and the amount of bupropion or pharmaceutically acceptable salt thereof is about 360 mg per day. In certain embodiments, the initial daily dose administered to the patient is about 4 mg or about 8 mg of the naltrexone or pharmaceutically acceptable salt thereof and about 90 mg of the bupropion or pharmaceutically acceptable salt thereof; and the daily dose administered to the patient for maintenance is about 16 mg or about 32 mg of the naltrexone or pharmaceutically acceptable salt thereof and about 360 mg of the bupropion or pharmaceutically acceptable salt thereof. In certain embodiments, the daily dose of the naltrexone or pharmaceutically acceptable salt thereof is a dosing schedule selected from the group consisting of 4 mg in week one to 8 mg in week two, 12 mg in week three, and 16 mg in week four and thereafter and 8 mg in week one to 16 mg in week two, 24 mg in week three, and 32 mg in week four and thereafter; and the daily dose of the bupropion or pharmaceutically acceptable salt thereof is escalated from 90 mg in week one to 180 mg in week two, 270 mg in week three, and 360 mg in week four and thereafter. In certain embodiments, the amount of naltrexone or pharmaceutically acceptable salt thereof is about 32 mg per day; and the amount of bupropion or pharmaceutically acceptable salt thereof is about 360 mg per day. In certain embodiments, the method further comprises adjusting the dosage of the naltrexone or pharmaceutically acceptable salt thereof, the bupropion or pharmaceutically acceptable salt thereof, or both as needed to treat the patient's major depressive disorder. In certain embodiments, the method further comprises adjusting the dosage of the naltrexone or pharmaceutically acceptable salt thereof, the bupropion or pharmaceutically acceptable salt thereof, or both as needed to treat the patient's overweight or obesity. In certain embodiments, at least one of the naltrexone or pharmaceutically acceptable salt thereof and bupropion or pharmaceutically acceptable salt thereof is in a sustained release formulation. In certain embodiments, each of the naltrexone or pharmaceutically acceptable salt thereof and bupropion or pharmaceutically acceptable salt thereof is in a sustained release formulation. In certain embodiments, the method further comprises administering the naltrexone or pharmaceutically acceptable salt thereof and bupropion or pharmaceutically acceptable salt thereof with food.

In some embodiments, a method for providing weight loss therapy to a patient is provided, comprising: identifying a patient suffering from major depressive disorder, wherein the patient is also overweight or obese; and reducing weight of the patient by administering to the patient naltrexone or a pharmaceutically acceptable salt thereof and bupropion or a pharmaceutically acceptable salt thereof, where the amount of the naltrexone or pharmaceutically acceptable salt thereof is about 32 mg per day; where the amount of the bupropion or pharmaceutically acceptable salt thereof is about 360 mg per day; and where each of the naltrexone or pharmaceutically acceptable salt thereof and bupropion or pharmaceutically acceptable salt thereof is in a sustained release formulation.

In some embodiments, a method for selecting a weight loss therapy from among available weight loss therapies is provided, comprising: evaluating a patient to assess whether the patient is simultaneously in need of weight loss therapy and depression therapy; and if so, providing to the patient an effective weight-loss-inducing and antidepressant combination of bupropion or a pharmaceutically acceptable salt thereof and naltrexone or a pharmaceutically acceptable salt thereof as active ingredients. In certain embodiments, the method further comprises providing printed information to the patient indicating that the combination promotes weight loss and reduces symptoms of depression. In certain embodiments, the patient has been diagnosed as suffering from major depressive disorder using the Montgomery-Åsberg Depression Rating Scale. In certain embodiments, the patient has been diagnosed as suffering from major depressive disorder using the Inventory of Depressive Symptomatology. In certain embodiments, the patient is not suffering from bipolar disorder. In certain embodiments, the patient has a body mass index of 25 kg/m$^2$ or above. In certain embodiments, the patient has a body mass index of 30 kg/m$^2$ or above. In certain embodiments, the patient is overweight. In certain embodiments, the patient is obese.

In certain embodiments, the patient is female. In certain embodiments, the weight-loss-inducing and antidepressant combination is administered at least once per day. In certain embodiments, the weight-loss-inducing and antidepressant combination is administered more than once per day. In certain embodiments, the weight-loss-inducing and antidepressant combination is administered for a period of at least 12 weeks. In certain embodiments, the weight-loss-inducing and antidepressant combination is administered for a period of at least 24 weeks. In certain embodiments, the naltrexone or pharmaceutically acceptable salt thereof is administered prior to or subsequent to the bupropion or pharmaceutically acceptable salt thereof. In certain embodiments, the naltrexone or pharmaceutically acceptable salt thereof and the bupropion or pharmaceutically acceptable salt thereof are in a single oral dosage form. In certain embodiments, the single oral dosage form further comprises a pharmaceutically acceptable excipient, diluent, or carrier. In certain embodiments, the amount of naltrexone or pharmaceutically acceptable salt thereof is about 5 mg to about 50 mg per day. In certain embodiments, the amount of bupropion or pharmaceutically acceptable salt thereof is about 30 mg to about 500 mg per day. In certain embodiments, the amount of the naltrexone or pharmaceutically acceptable salt thereof is about 5 mg to about 50 mg per day; and the amount of the bupropion or pharmaceutically acceptable salt thereof is about 30 mg to about 500 mg per day. In certain embodiments, the amount of the naltrexone or pharmaceutically acceptable salt thereof is about 4 mg to about 50 mg per day; and the amount of the bupropion or pharmaceutically acceptable salt thereof is about 30 mg to about 500 mg per day. In certain embodiments, the amount of naltrexone or pharmaceutically acceptable salt thereof is about 16 mg or about 32 mg per day; and the amount of bupropion or pharmaceutically acceptable salt thereof is about 360 mg per day. In certain embodiments, the initial daily dose administered to the patient is about 4 mg or about 8 mg of the naltrexone or pharmaceutically acceptable salt thereof and about 90 mg of the bupropion or pharmaceutically acceptable salt thereof; and the daily dose administered to the patient for maintenance is about 16 mg or about 32 mg of the naltrexone or pharmaceutically acceptable salt thereof and about 360 mg of the bupropion or pharmaceutically acceptable salt thereof. In certain embodiments, the daily dose of the naltrexone or pharmaceutically acceptable salt thereof is a dosing schedule selected from the group consisting of 4 mg in week one to 8 mg in week two, 12 mg in week three, and 16 mg in week four and thereafter and 8 mg in week one to 16 mg in week two, 24 mg in week three, and 32 mg in week four and thereafter; and the daily dose of the bupropion or pharmaceutically acceptable salt thereof is escalated from 90 mg in week one to 180 mg in week two, 270 mg in week three, and 360 mg in week four and thereafter. In certain embodiments, the amount of naltrexone or pharmaceutically acceptable salt thereof is about 32 mg per day; and the amount of bupropion or pharmaceutically acceptable salt thereof is about 360 mg per day. In certain embodiments, the method further comprises adjusting the dosage of the naltrexone or pharmaceutically acceptable salt thereof, the bupropion or pharmaceutically acceptable salt thereof, or both as needed to treat the patient's major depressive disorder. In certain embodiments, the method further comprises adjusting the dosage of the naltrexone or pharmaceutically acceptable salt thereof, the bupropion or pharmaceutically acceptable salt thereof, or both as needed to treat the patient's overweight or obesity. In certain embodiments, at least one of the naltrexone or pharmaceutically acceptable salt thereof and bupropion or pharmaceutically acceptable salt thereof is in a sustained release formulation. In certain embodiments, each of the naltrexone or pharmaceutically acceptable salt thereof and bupropion or pharmaceutically acceptable salt thereof is in a sustained release formulation. In certain embodiments, the method further comprises administering the naltrexone or pharmaceutically acceptable salt thereof and bupropion or pharmaceutically acceptable salt thereof with food.

In some embodiments, a method for providing weight loss therapy to a patient is provided, comprising: providing to the patient a drug product comprising an effective weight-loss inducing combination of bupropion or a pharmaceutically acceptable salt thereof and naltrexone or a pharmaceutically acceptable salt thereof as active ingredients; and providing to the patient printed information indicating that in depressed patients, the drug product results in a promotion of weight loss and a reduction of symptoms of depression. In certain embodiments, the patient has been diagnosed as suffering from major depressive disorder using the Montgomery-Åsberg Depression Rating Scale. In certain embodiments, the patient has been diagnosed as suffering from major depressive disorder using the Inventory of Depressive Symptomatology. In certain embodiments, the patient is not suffering from bipolar disorder. In certain embodiments, the patient has a body mass index of 25 kg/m² or above. In certain embodiments, the patient has a body mass index of 30 kg/m² or above. In certain embodiments, the patient is overweight. In certain embodiments, the patient is obese. In certain embodiments, the patient is female. In certain embodiments, the drug product is administered at least once per day. In certain embodiments, the drug product is administered more than once per day. In certain embodiments, the drug product is administered for a period of at least 12 weeks. In certain embodiments, the drug product is administered for a period of at least 24 weeks. In certain embodiments, the naltrexone or pharmaceutically acceptable salt thereof is administered prior to or subsequent to the bupropion or pharmaceutically acceptable salt thereof. In certain embodiments, the naltrexone or pharmaceutically acceptable salt thereof and the bupropion or pharmaceutically acceptable salt thereof are in a single oral dosage form. In certain embodiments, the single oral dosage form further comprises a pharmaceutically acceptable excipient, diluent, or carrier. In certain embodiments, the amount of naltrexone or pharmaceutically acceptable salt thereof is about 5 mg to about 50 mg per day. In certain embodiments, the amount of bupropion or pharmaceutically acceptable salt thereof is about 30 mg to about 500 mg per day. In certain embodiments, the amount of the naltrexone or pharmaceutically acceptable salt thereof is about 5 mg to about 50 mg per day; and the amount of the bupropion or pharmaceutically acceptable salt thereof is about 30 mg to about 500 mg per day. In certain embodiments, the amount of the naltrexone or pharmaceutically acceptable salt thereof is about 4 mg to about 50 mg per day; and the amount of the bupropion or pharmaceutically acceptable salt thereof is about 30 mg to about 500 mg per day. In certain embodiments, the amount of naltrexone or pharmaceutically acceptable salt thereof is about 16 mg or about 32 mg per day; and the amount of bupropion or pharmaceutically acceptable salt thereof is about 360 mg per day. In certain embodiments, the initial daily dose administered to the patient is about 4 mg or about 8 mg of the naltrexone or pharmaceutically acceptable salt thereof and about 90 mg of the bupropion or pharmaceutically acceptable salt thereof; and the daily dose administered to the patient for maintenance is about 16 mg or about 32 mg of the naltrexone or pharmaceutically acceptable salt thereof and about 360 mg of the bupropion or pharmaceutically acceptable salt thereof. In certain embodiments, the daily dose of the naltrexone or pharmaceutically acceptable salt thereof is a dosing schedule selected from the group consisting of 4 mg in week one to 8 mg in week two, 12 mg in week three, and 16 mg in week four and thereafter and 8 mg in week one to 16 mg in week two, 24 mg in week three, and 32 mg in week four and thereafter; and the daily dose of the bupropion or pharmaceutically acceptable salt thereof is escalated from 90 mg in week one to 180 mg in week two, 270 mg in week three, and 360 mg in week four and thereafter. In certain embodiments, the amount of naltrexone or pharmaceutically acceptable salt thereof is about 32 mg per day; and the amount of bupropion or pharmaceutically acceptable salt thereof is about 360 mg per day. In certain embodiments, the method further comprises adjusting the dosage of the naltrexone or pharmaceutically acceptable salt thereof, the bupropion or pharmaceutically acceptable salt thereof, or both as needed to treat the patient's major depressive disorder. In certain embodiments, the method further comprises adjusting the dosage of the naltrexone or pharmaceutically acceptable salt thereof, the bupropion or pharmaceutically acceptable salt thereof, or both as needed to treat the patient's overweight or obesity. In certain embodiments, at least one of the naltrexone or pharmaceutically acceptable salt thereof and bupropion or pharmaceutically acceptable salt thereof is in a sustained release formulation. In certain embodiments, each of the naltrexone or pharmaceutically acceptable salt thereof and bupropion or pharmaceutically acceptable salt thereof is in a sustained release formulation. In certain embodiments, the method further comprises administering the naltrexone or pharmaceutically acceptable salt thereof and bupropion or pharmaceutically acceptable salt thereof with food.

DETAILED DESCRIPTION OF THE PREFERRED EMBODIMENT

In some embodiments, the method is effective to reduce the symptoms of major depression. In some embodiments, the reduction in symptoms of major depression is measured by a percent change from baseline symptoms before treatment. In some embodiments, the reduction in symptoms of major depression is measured by a change in a Montgomery-Åsberg Depression Rating Scale score. In some embodiments, the reduction in symptoms of major depression is measured by a change in an Inventory of Depressive Symptomatology-Self Report (IDS-SR) score. In some embodiments, the reduction in symptoms of major depression is measured by a change as assessed by the Clinical Global Impressions-Improvement (CGI-I) scale. In some of these embodiments, the reduction in symptoms of major depression is measured by a change in response and/or remission rates of depressive symptoms. In a preferred embodiment, the reduction in symptoms of major depression is at least about 40%. In some embodiments, the reduction in symptoms of major depression is, is about, is at least, is at least about 2%, 5%, 10%, 15%, 20%, 25%, 30%, 35%, 40%, 45%, 50%, 55%, 60%, 65%, 70%, 75%, 80%, 85%, 90%, 95%, or 100%, or a range defined by any two of the preceding values. In some embodiments, a reduction in symptoms of major depression is seen at about 4, 8, 12, 16, 20, 24, 36, 48, or 52 weeks, or a range defined by any two of the preceding values.

In some embodiments, the method is effective to promote weight loss or mitigate weight gain in an overweight or obese individual. In some embodiments, the individual has gained weight as a result of depression and/or as a result of being administered another drug product for the treatment of depression. However, in some embodiments, the cause of the individual's overweight or obesity is unknown. In some embodiments, a method of promoting weight loss or mitigating weight gain and reducing symptoms of major depression is provided. In some embodiments, a method of reducing symptoms of major depression is provided regardless of weight loss or mitigation of weight gain. In some embodiments, a method of promoting weight loss or mitigating weight gain is provided regardless of a reduction in symptoms of major depression.

In some embodiments, the individual has a body mass index (BMI) of at least 25 kg/m$^2$. In some embodiments, the individual has a BMI of at least 30 kg/m$^2$. In some embodiments, the individual has a BMI of at least 40 kg/m$^2$. In some embodiments, the individual has a BMI of less than 25 kg/m$^2$, or develops a BMI less than 25 kg/m$^2$ during the course of administration of naltrexone and bupropion. In these embodiments, it may be beneficial for health or cosmetic purposes to mitigate subsequent weight gain or to promote weight loss, thereby reducing the BMI even further. In some embodiments, the individual has been diagnosed by a physician as being overweight or obese. In some embodiments, the individual is identified, including self-identified, as overweight or obese, or is identified as having been diagnosed as overweight or obese.

In some embodiments, the promotion of weight loss is measured by a percent change from a baseline body weight. In some of these embodiments, the amount of weight loss is, is about, is at least, is at least about 0.5%, 1%, 1.5%, 2%, 2.5%, 3%, 4%, 5%, 6%, 7%, 8%, 9%, 10%, 12%, 15%, or more of initial body weight, or a range defined by any two of the preceding values. In some embodiments, the promotion of weight loss is measured as a reduction in weight gain relative to the amount of weight gain experienced when neither or only one of naltrexone and bupropion is administered, and the amount of reduction in weight gain is, is about, is at least, is at least about, 2%, 5%, 10%, 15%, 20%, 25%, 30% 40%, 50%, 60%, 70%, 80%, 90%, 100%, 105%, 110%, 115%, 120%, or more, or a range defined by any two of the preceding values.

In some embodiments, the mitigation of weight gain is measured by a percent change from a baseline body weight. In some of these embodiments, the amount of weight gain is, is about, is not more than, is not more than about 0%, 0.5%, 1%, 1.5%, 2%, 2.5%, 3%, 4%, 5%, 6%, 7%, 8%, 9%, 10% or more of initial body weight, or a range defined by any two of the preceding values.

In some embodiments, the dosage is adjusted so that the patient loses weight at a rate of about 3% of baseline body weight every six months. However, the rate of weight loss for a patient may be adjusted by the treating physician based on the patient's particular needs. In some embodiments, the dosage is adjusted so that the patient exhibits a 50% reduction in symptoms of depression every six months. However, the rate of reduction in symptoms of depression for a patient may also be adjusted by the treating physician based on the patient's particular needs.

In some embodiments, the mitigation of weight gain or promotion of weight loss occurs by increasing satiety in the individual. In some embodiments, the mitigation of weight gain or promotion of weight loss occurs by suppressing the appetite of the individual. In some embodiments, the individual receives depression or weight loss counseling, or both. In some embodiments, the method further comprises instituting a regimen of diet and/or increased activity. In some embodiments, the individual is co-administered another drug product for the treatment of depression. For example, in some embodiments, the individual is co-administered venlafaxine, duloxetine, or aripiprazole.

In some embodiments, treatment of an obese person undergoing or about to begin a period of treatment for depression results in greater mitigation of weight gain or promotion of weight loss than that observed when treating an overweight or normal weight person undergoing or about to begin treatment for depression. In some embodiments, treatment of an obese person undergoing or about to begin a period of treatment for depression results in greater mitigation of weight gain or promotion of weight loss than that observed when treating an obese or overweight person not suffering from depression with bupropion and naltrexone.

In some embodiments, treatment of an overweight person undergoing or about to begin a period of treatment for depression results in greater mitigation of weight gain or promotion of weight loss than that observed when treating an obese or normal weight person undergoing or about to begin treatment for depression. In some embodiments, treatment of an overweight person undergoing or about to begin a treatment for depression results in greater mitigation of weight gain or promotion of weight loss than that observed when treating an obese or overweight person not suffering from depression with bupropion and naltrexone.

In some embodiments, the treatment works as well or better for treating obesity or overweight in an obese or overweight person suffering from major depression as it does for an obese, overweight, or normal weight person not suffering from major depression. For example, in some embodiments, the treatment results in the same weight loss in an obese or overweight person suffering from depression as it would in an obese or overweight person not suffering from depression. In some embodiments, the treatment results in greater weight loss in an obese or overweight person suffering from depression as it would in an obese or overweight person not suffering from depression.

In some embodiments, the treatment works as well or better for treating depression in an obese or overweight person suffering from major depression as it does for a normal weight person suffering from major depression. For example, in some embodiments, the treatment results in the same reduction in symptoms of depression for an obese or overweight person as it would in a normal weight person. In some embodiments, the treatment results in a greater reduction in the symptoms of depression in an obese or overweight person suffering from depression as it would in a normal weight person suffering from depression.

In some embodiments, naltrexone and bupropion are each administered once per day. In some embodiments, naltrexone and bupropion are each divided into equal doses and administered more than once per day. In some embodiments, naltrexone and bupropion are each divided into unequal doses and administered more than once per day. In some embodiments, naltrexone and bupropion are divided into a different number of doses and are administered a different number of times per day. In one such embodiment, the dose of one of naltrexone or bupropion is divided, while the dose of the other is not.

In some embodiments, one or both of naltrexone and bupropion is administered one, two, three, four, or more times per day. In some embodiments, one or both of naltrexone and bupropion are administered in a controlled release formulation. Either or both compounds can be administered less than once per day, for example once every 2, 3, 4, 5, 6, 7, 8, 9, 10, 11, 12, 13, or 14 days, or every 1 or 2 weeks, or a range defined by any two of the preceding values.

The exact formulation, route of administration, and dosage for naltrexone and bupropion combinations described herein can be chosen by the individual physician in view of the patient's condition. (See e.g., Fingl et al. 1975, in "The Pharmacological Basis of Therapeutics," Ch. 1 p. 1). In some embodiments, the daily dose of naltrexone and bupropion is the same, and in some embodiments, the daily dose is different.

In some embodiments, the daily dose of naltrexone can range from about 4 mg to about 50 mg, or about 4 mg to about 32 mg, or about 8 mg to about 32 mg, or about 8 mg to about 16 mg. In some embodiments, the daily dose is about 4 mg, about 8 mg, about 12 mg, about 16 mg, about 32 mg, or about 48 mg of naltrexone, or a range defined by any two of the preceding values. In some embodiments, the daily dose is administered in a single oral dosage form. The selection of a particular dosage may be based on the weight of the patient. The selection of a particular dosage may be based on the identity, dosage, and/or dosing schedule of another co-administered compound. However, in some embodiments, it may be necessary to use dosages outside these ranges.

In some embodiments, the daily dose of bupropion can range from about 30 mg to about 500 mg, or about 30 mg to about 360 mg, or about 90 mg to about 360 mg. In some embodiments, the daily dose is about 30 mg, about 90 mg, about 180 mg, about 360 mg, or about 450 mg of bupropion, or a range defined by any two of the preceding values. In some embodiments, the daily dose is administered in a single oral dosage form. The selection of a particular dosage may be based on the weight of the patient. The selection of a particular dosage may be based on the identity, dosage and/or dosing schedule of another co-administered compound. However, in some embodiments, it may be necessary to use dosages outside these ranges.

In some embodiments, at least one of naltrexone and bupropion is administered with varying frequency during treatment. In some of these embodiments, the varying frequency comprises a decreased frequency over time. For example, one or both of naltrexone and bupropion can be initially administered more than once per day, followed by administration only once per day at a later point in treatment. In some embodiments, the daily dosage of at least one of naltrexone and bupropion is consistent despite the varying frequency of administration. For example, in some embodiments, two tablets of each of naltrexone and bupropion are initially administered twice per day, while four tablets of each of naltrexone and bupropion are administered once per day at a later point in treatment. Alternatively, in some embodiments, one or two tablets of each of naltrexone and bupropion are administered at a later point in treatment, where the one or two tablets have an equivalent total daily dosage as the two tablets each of naltrexone and bupropion initially administered twice per day.

In some embodiments where one or both of naltrexone and bupropion are administered less than once per day in a controlled release or sustained release (SR) formulation, the dose is selected so that the patient receives a daily dose that is about the same as a daily dose described herein.

In some embodiments, at least one of naltrexone or bupropion is administered in consistent daily dosages throughout the period of treatment. In some embodiments, at least one of naltrexone or bupropion is administered in varying daily dosages during the period of treatment. In some of these embodiments, the daily dosages comprise increasing daily dosages over time. In some of these embodiments, the daily dosages comprise decreasing daily dosages over time.

In some embodiments, naltrexone and bupropion are administered individually. In some embodiments, naltrexone and bupropion are administered in a single pharmaceutical composition comprising naltrexone and bupropion. In some embodiments, at least one of naltrexone or bupropion is in a sustained release or controlled release formulation. For example, sustained release forms of naltrexone are described in U.S. Patent Publication No. 2007/0281021, which is incorporated herein by reference in its entirety and for all purposes, including without limitation for the purpose of describing sustained release forms of naltrexone and bupropion, methods of making and formulating them into suitable dosage forms, and methods of administering them. In some embodiments, at least one of naltrexone or bupropion is administered with a physiologically acceptable carrier, diluent, or excipient, or a combination thereof. Non-limiting examples of naltrexone/bupropion combinations, formulations thereof, and methods of administering them are disclosed in U.S. Pat. Nos. 7,375,111 and 7,462,626, both of which are incorporated herein by reference in their entirety and for all purposes, including without limitation for the purpose of describing combinations of naltrexone and bupropion, methods of making and formulating them into suitable dosage forms, and methods of administering them. Reference herein to the use or administration of naltrexone/bupropion combinations will be understood to include all modes of administration disclosed or referred to herein, including without limitation separate administration, administration in a single dosage form, administration in the form of salts, prodrugs and/or metabolites, and/or administration in sustained release forms. Techniques for formulation and administration of the compounds of the instant application may be found in "Remington's Pharmaceutical Sciences," Mack Publishing Co., Easton, Pa., 18th edition, 1990, which is incorporated herein by reference in its entirety.

In some embodiments, naltrexone is administered prior to the bupropion. In some embodiments, naltrexone is administered subsequent to the bupropion. In some embodiments, naltrexone and the bupropion are co-administered. As used herein, co-administration includes administration in a single dosage form, or separate dosage forms that are administered at, or nearly at, the same time.

In some embodiments, the administration of naltrexone and bupropion is continued for a period of, or of about, 4, 12, 16, 20, 24, 36, 48, or 52 weeks, or a range defined by any two of the preceding values. In some embodiments, the administration of naltrexone and bupropion is continued until the reduction in symptoms of depression is stabilized for a period of, or of about, 1, 2, 3, 4, 5, 6, or more weeks, or a range defined by any two of the preceding values. In some embodiments, the administration of naltrexone and bupropion is continued until the mitigation of weight gain or promotion of weight loss is stabilized for a period of, or of about, 1, 2, 3, 4, 5, 6, or more weeks, or a range defined by any two of the preceding values. In some embodiments, administration of naltrexone and bupropion is continued until the individual no longer needs treatment for major depressive disorder. In some embodiments, administration of naltrexone and bupropion is continued until the individual no longer needs treatment for obesity or overweight.

The compositions described herein may, if desired, be presented in a pack or dispenser device which may contain one or more unit dosage forms containing one or both of the active ingredients. The pack may, for example, comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition. Non-limiting examples of packs and dispensers as well as oral dosage forms are disclosed in U.S. Patent Publication Nos. 2008-0110792 and 2008-0113026, both of which are hereby incorporated herein by reference in their entirety and for all purposes, including without limitation for the purpose of describing combinations of naltrexone and bupropion, methods of making and formulating them into suitable dosage forms, methods of packing and dispensing them, and methods of administering them.

In some embodiments, the single oral dosage form comprises a plurality of layers. For example, in some embodiments, the single oral dosage form is a trilayer tablet with a first pharmaceutical layer, a second pharmaceutical layer, and an intermediate layer disposed between the first and second pharmaceutical layers that is configured to rapidly dissolve in vivo. Non-limiting examples of multilayer tablets are disclosed in U.S. Patent Application Nos. 2008-0110792 and 2008-0113026, both of which are hereby incorporated herein by reference in their entirety and for all purposes.

Instructions and/or information may be present in a variety of forms, including printed information on a suitable medium or substrate (e.g., a piece or pieces of paper on which the information is printed), computer readable medium (e.g., diskette, CD, etc., on which the information has been recorded), or a website address that may be accessed via the internet. Printed information may, for example, be provided on a label associated with a drug product, on the container for a drug product, packaged with a drug product, or separately given to the patient apart from a drug product, or provided in manner that the patient can independently obtain the information (e.g., a website). Printed information may also be provided to a medical caregiver involved in treatment of the patient.

Throughout the present disclosure, when a particular compound is mentioned by name, for example, bupropion or naltrexone, it is understood that the scope of the present disclosure encompasses pharmaceutically acceptable salts, esters, amides, metabolites, or prodrugs of the named compound. For example, in any of the embodiments herein, an active metabolite of naltrexone, e.g., 6-β naltrexol, can be used in combination with, or instead of, naltrexone. In any of the embodiments herein, an active metabolite of bupropion, including S,S-hydroxybupropion (i.e., radafaxine), can be used in combination with, or instead of, bupropion.

As used herein, "mitigate" or "mitigation" of weight gain includes preventing or decreasing the amount of weight gain associated with depression or with the administration of another drug therapy for depression. In some embodiments, mitigation is measured relative to the amount of weight gain typically experienced when only one or neither of naltrexone or bupropion is administered.

As used herein, "promotion" of weight loss includes causing weight loss relative to a baseline weight for a least a portion of the period of treatment. This includes an individual that initially gains some weight, but during the course of treatment loses weight relative to a baseline prior to beginning treatment, as well as individuals that regain a portion or all of the weight that is lost by the end of the treatment period. In a preferred embodiment, at the end of the treatment period, the individual has lost weight relative to a baseline. In a preferred embodiment, mitigation of weight gain or promotion of weight loss in a patient administered naltrexone and bupropion is greater than when neither or only one of naltrexone or bupropion is administered, and more preferably an at least additive, or better than additive, or synergistic, effect of administering the two compounds is achieved.

The term "pharmaceutically acceptable salt" refers to a formulation of a compound that does not cause significant irritation to an organism to which it is administered and does not abrogate the biological activity and properties of the compound. Pharmaceutical salts can be obtained by routine experimentation. Non-limiting examples of pharmaceutically acceptable salts include bupropion hydrochloride, radafaxine hydrochloride, naltrexone hydrochloride, and 6-β naltrexol hydrochloride.

A "prodrug" refers to an agent that is converted into the parent drug in vivo. Prodrugs are often useful because, in some situations, they may be easier to administer than the parent drug. They may, for instance, be bioavailable by oral administration to a greater extent than the parent. The prodrug may also have improved solubility in pharmaceutical compositions over the parent drug, demonstrate increased palatability, or be easier to formulate. Non-limiting examples of suitable prodrugs include those described in U.S. Patent Publication No. 2007/0117827, which is incorporated herein by reference in its entirety and for all purposes, including without limitation for the purposes of describing naltrexone metabolites and prodrugs thereof, methods of making and formulating them into suitable dosage forms, and methods of administering them.

It will be understood by those of skill in the art that numerous and various modifications can be made without departing from the spirit of the present invention. Therefore, it should be clearly understood that the embodiments of the present invention disclosed herein are illustrative only and are not intended to limit the scope of the present invention. Any reference referred to herein is incorporated by reference for the material discussed herein, and in its entirety.

EXAMPLES

The examples below are non-limiting and are merely representative of various aspects of the invention.

Example 1

Naltrexone and Bupropion

A 24-week open label study of sustained release naltrexone (naltrexone SR) plus sustained release bupropion (bupropion SR) for depression and minimization of weight gain in subjects with BMI≥27 and ≤43 kg/m$^2$ was performed according to the dose escalation schedule provided in Table 1. All subjects met the DSM-IV criteria for major depression (without psychotic features) and had an IDS-SR total score≥26.

TABLE 1

| | Morning Dose | Evening Dose | Total Daily Dose |
|---|---|---|---|
| Week 1 | one tablet (8 mg naltrexone SR + 90 mg bupropion SR/tablet) | — | 8 mg naltrexone SR/90 mg bupropion SR |
| Week 2 | one tablet (8 mg naltrexone SR + 90 mg bupropion SR/tablet) | one tablet (8 mg naltrexone SR + 90 mg bupropion SR/tablet) | 16 mg naltrexone SR/180 mg bupropion SR |
| Week 3 | two tablets (8 mg naltrexone SR + 90 mg bupropion SR/tablet) | one tablet (8 mg naltrexone SR + 90 mg bupropion SR/tablet) | 24 mg naltrexone SR/270 mg bupropion SR |
| Week 4-Onward | two tablets (8 mg naltrexone SR + 90 mg bupropion SR/tablet) | two tablets (8 mg naltrexone SR + 90 mg bupropion SR/tablet) | 32 mg naltrexone SR/360 mg bupropion SR |

The primary outcomes were percent and absolute change from baseline in total body weight and subject-reported depression at weeks 12 and 24. Other efficacy measures were: change in waist circumference; serum leptin and ghrelin levels; creatinine levels; and safety and tolerability. Adverse events and vital signs (e.g., systolic and diastolic blood pressure and pulse) were used to monitor safety and tolerability. Of the 25 subjects enrolled, all were female, 23 were Caucasian, and the average age was 47. All 25 subjects provided at least one post-baseline evaluation, and 14 and 12 of the subjects completed 12 and 24 weeks of treatment, respectively.

MADRS total scores decreased from 23.65 to 10.52 and 8.35 at weeks 12 and 24, respectively. IDS-SR total scores decreased from 43.20 to about 23 and 16 at weeks 12 and 24, respectively. CGI-I response rates were 90.0% and 95.0% at weeks 12 and 24, respectively, as measured by full analysis set, last observation carried forward (FAS LOCF). CGI-I remission rates were 55.0% and 70.0% at weeks 12 and 24, respectively, as measured by FAS LOCF. Total body weight decreased by 4.42% and 5.86% at weeks 12 and 24, respectively, as measured by FAS LOCF, and 6.75% and 9.96% at weeks 12 and 24, respectively, as measured by observed case (OC) analysis. The most common adverse events were nausea, constipation, headache, insomnia, dizziness, and hot flush. In overweight or obese subjects, naltrexone plus bupropion reduced symptoms of depression while preventing weight gain.

Example 2

Naltrexone and Bupropion

Patients having a BMI of greater than 25 are identified. Each patient is instructed to take two 8 mg tablets of naltrexone (SR) twice daily, in addition to two 90 mg tablets of bupropion (SR) twice daily.

The patients are monitored for a period of months. It is recommended that the dosage be adjusted so that each patient loses weight at a rate of at least about 3% of initial weight and exhibits a 50% reduction in symptoms of depression every six months. However, the rate of weight loss and reduction in symptoms of depression for each patient may be adjusted by the treating physician based on the patient's particular needs.

If the initial dosage is not effective, then the dosage of either or both of naltrexone and bupropion can be increased. Alternatively, if the initial dosage results in a more rapid weight loss or reduction in symptoms of depression than the above rates, the dosage of either or both of naltrexone and bupropion can be reduced.

Example 3

Naltrexone and Bupropion

In a multicenter, randomized, blinded, placebo-controlled clinical trial, the following drug combinations are tested:
  Group 1—naltrexone (SR) 16 mg po BID+bupropion (SR) 180 mg po BID
  Group 2—N-placebo po BID+bupropion (SR) 180 mg po BID
  Group 3—P-placebo po BID+naltrexone (SR) 16 mg po BID
  Group 4—N-placebo po BID+P-placebo po BID.

In any of the above groups, the dosage of naltrexone may be administered in doses in the range between 5 mg and 50 mg, for example, 5 mg, 10 mg, 15 mg, 20 mg, 25 mg, 30 mg, 35 mg, 40 mg, 45 mg, and 50 mg. In any of the above groups, the dosage of bupropion may be administered in doses in the range between 30 mg and 500 mg, for example, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, and 500 mg.

The primary endpoints are percent and absolute change from baseline in total body weight and subject-reported depression at weeks 12 and 24. Secondary endpoints include percent and absolute change from baseline in total body weight at weeks 36 and 48, change in waist circumference; serum leptin and ghrelin levels; creatinine levels; and safety and tolerability. Adverse events, laboratory parameters, and vital signs are used to monitor safety and tolerability.

What is claimed is:

1. A method for providing weight loss therapy to a patient, comprising:
   identifying an overweight or obese patient who is suffering from major depressive disorder; and
   reducing weight of the patient by administering to the patient a pharmaceutical weight loss therapy comprising naltrexone or a pharmaceutically acceptable salt thereof and bupropion or a pharmaceutically acceptable salt thereof, wherein the amount of naltrexone or pharmaceutically acceptable salt thereof is about 32 mg per day and the amount of the bupropion or pharmaceutically acceptable salt thereof is about 360 mg per day, and wherein said method provides about the same amount of weight loss in overweight or obese patients who are suffering from major depressive disorder as in overweight or obese patients who are not suffering from major depressive disorder.

2. The method of claim 1, further comprising reducing symptoms of depression in the patient.

3. The method of claim 1, wherein the patient is overweight.

4. The method of claim 1, wherein the patient is obese.

5. The method of claim 1, wherein the naltrexone or a pharmaceutically acceptable salt thereof and bupropion or a pharmaceutically acceptable salt thereof is administered once per day.

6. The method of claim 1, wherein the naltrexone or a pharmaceutically acceptable salt thereof and bupropion or a pharmaceutically acceptable salt thereof is administered more than once per day.

7. The method of claim 1, wherein the naltrexone or pharmaceutically acceptable salt thereof is administered prior to or subsequent to the bupropion or pharmaceutically acceptable salt thereof.

8. The method of claim 1, wherein the naltrexone or pharmaceutically acceptable salt thereof and the bupropion or pharmaceutically acceptable salt thereof are in a single oral dosage form.

9. The method of claim 8, wherein the single oral dosage form further comprises a pharmaceutically acceptable excipient, diluent, or carrier.

10. The method of claim 1, wherein the daily dose of the naltrexone or pharmaceutically acceptable salt thereof is escalated from 8 mg in week one to 16 mg in week two, 24 mg in week three, and 32 mg in week four and thereafter; and wherein the daily dose of the bupropion or pharmaceutically acceptable salt thereof is escalated from 90 mg in week one to 180 mg in week two, 270 mg in week three, and 360 mg in week four and thereafter.

11. The method of claim 10, wherein at least one of the naltrexone or pharmaceutically acceptable salt thereof and bupropion or pharmaceutically acceptable salt thereof is in a sustained release formulation.

12. The method of claim 11, wherein the naltrexone or pharmaceutically acceptable salt thereof and the bupropion or pharmaceutically acceptable salt thereof are in a single oral dosage form.

13. The method of claim 10, wherein each of the naltrexone or pharmaceutically acceptable salt thereof and bupropion or pharmaceutically acceptable salt thereof is in a sustained release formulation.

14. The method of claim 13, wherein the naltrexone or pharmaceutically acceptable salt thereof and the bupropion or pharmaceutically acceptable salt thereof are in a single oral dosage form.

15. The method of claim 1, wherein at least one of the naltrexone or pharmaceutically acceptable salt thereof and bupropion or pharmaceutically acceptable salt thereof is in a sustained release formulation.

16. The method of claim 1, wherein each of the naltrexone or pharmaceutically acceptable salt thereof and bupropion or pharmaceutically acceptable salt thereof is in a sustained release formulation.

17. The method of claim 1, wherein the pharmaceutical weight loss therapy consists essentially of naltrexone or a pharmaceutically acceptable salt thereof and bupropion or a pharmaceutically acceptable salt thereof.

18. The method of claim 1, wherein said method further reduces the symptoms of depression in the patient.

* * * * *